(12) United States Patent
Inoue

(10) Patent No.: US 6,949,615 B2
(45) Date of Patent: Sep. 27, 2005

(54) MONOMER HAVING ELECTRON-WITHDRAWING GROUP AND PROCESS FOR PREPARING THE SAME

(75) Inventor: Keizo Inoue, Himeji (JP)

(73) Assignee: Daicel Chemical Industries, Ltd., Osaka (JP)

( * ) Notice: Subject to any disclaimer, the term of this patent is extended or adjusted under 35 U.S.C. 154(b) by 147 days.

(21) Appl. No.: 10/181,830

(22) PCT Filed: Oct. 31, 2001

(86) PCT No.: PCT/JP01/09530

§ 371 (c)(1),
(2), (4) Date: Jul. 23, 2002

(87) PCT Pub. No.: WO02/36533

PCT Pub. Date: May 10, 2002

(65) Prior Publication Data

US 2003/0059710 A1 Mar. 27, 2003

(30) Foreign Application Priority Data

Oct. 31, 2000   (JP) ..................... 2000-331602

(51) Int. Cl.⁷ ............................................. C08F 114/18
(52) U.S. Cl. ....................... 526/242; 526/266; 526/247
(58) Field of Search ................................. 526/266, 242, 526/247

(56) References Cited

U.S. PATENT DOCUMENTS 2,928,865 A * 3/1960 Brasen ....................... 558/366

FOREIGN PATENT DOCUMENTS

| EP | 0 157262 | * | 9/1985 |
|---|---|---|---|
| EP | 0 157 262 A1 | | 10/1985 |
| JP | 64-22866 A | | 1/1989 |
| JP | 02-004722 | * | 1/1990 |
| WO | WO 00/17712 | * | 3/2000 |

OTHER PUBLICATIONS

Cho et al., "Negative tone 193 nm resists", Proceedings of SPIE, 3999, 62–69(2000).*
Chiba et al., "157 nm resist materials: a progress report", Journal of photopolymer science and technology, 13(4), 657–664(2000).*
Ito et al., Polym. Mater. Sci. Eng., 77, 449–450 (1997).*
Chiba et al., J. of photopolymer Science and Technology, 13(4),657–664(2000).*
Ito et al., ACS Symposium Series, 706, 208–223 (1998).*
Cho et al., Adv. in Resist Technologyand Processing XVII, Proceedings of SPIE, 3999, 62–73(2000).*
Huque et al., J. Chem. Res., Synop. No. 7, pp. 214 (1987).
Snatzke et al., Chem. Ber., vol. 105, No. 1, pp. 244–256 (1972).

(Continued)

Primary Examiner—Ling-Sui Choi
(74) Attorney, Agent, or Firm—Birch, Stewart, Kolasch & Birch, LLP

(57) ABSTRACT

A monomer containing an electron-withdrawing group of the present invention is represented by following Formula (a), (b) or (c):

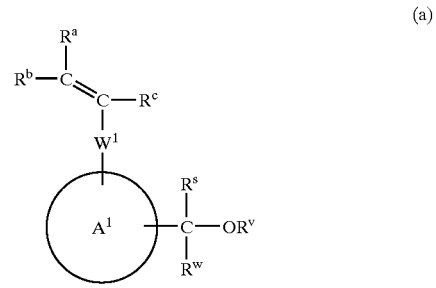

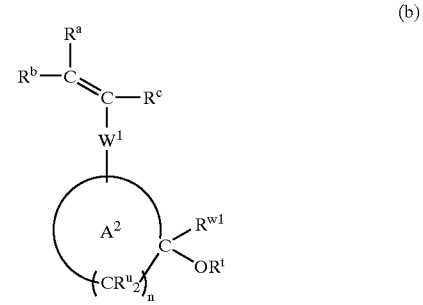

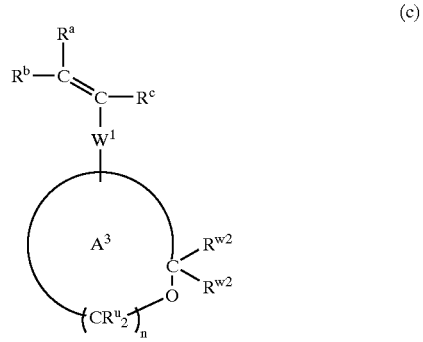

wherein $A^1$, $A^2$, and $A^3$ are each a ring; $R^a$, $R^b$, $R^c$, and $R^u$ are the same or different and are each a hydrogen atom or organic group; at least one of $R^s$, $R^w$ and $R^v$, at least one of $R^t$ and $R^{w1}$, and at least one of the two $R^{w2}$s are each an electron-withdrawing group, and the others are each a hydrogen atom or organic group; $W^1$ is a single bond or linkage group; and n denotes an integer of 2 to 25, where at least two of $R^a$, $R^b$, $R^c$, $R^s$, $R^t$, $R^u$, $R^v$, $R^w$, $R^{w1}$, $R^{w2}$, $W^1$, and carbon atoms constituting ring $A^1$, carbon atoms constituting ring $A^2$, and carbon atoms constituting ring $A^3$ may be combined to form a ring, respectively. The electron-withdrawing groups in $R^s$, $R^t$, $R^v$, $R^w$, $R^{w1}$, and $R^{w2}$ are, for example, groups each containing a fluorine atom. The monomer is useful as a raw material for photoresist polymeric compounds.

12 Claims, No Drawings

OTHER PUBLICATIONS

Dua et al., J. Chem. Soc., Perkin Trans. 2, No. 6, pp. 1443–1448 (1998).
Shono et al., Chem. Lett., No. 1, pp. 69–72 (1979).
Hartke et al., Liebigs Ann. Chem., No. 11, pp. 1665–1676 (1980).
Laduron et al., J. Prakt. Chem./Chem.—Ztg., vol. 339, No. 8, pp. 697–707 (1997).
Burdon et al., Tetrahedron, vol. 27, No. 19, pp. 4533–4551 (1971).
Ito et al., Polym. Mater. Sci. Eng., No. 77, pp. 449–450 (1997).
Morihira et al., Bioorg. Med. Chem. Lett., vol. 8, No. 21, pp. 2977–2982 (1998).
Vedejs et al., J. Org. Chem, vol. 44, No. 18, pp. 3230–3238 (1979).

* cited by examiner

MONOMER HAVING ELECTRON-WITHDRAWING GROUP AND PROCESS FOR PREPARING THE SAME

This application is the national phase under 35 U.S.C. § 371 of PCT International Application No. PCT/JP01/09530 which has an International filing date of Oct. 31, 2001, which designated the United States of America.

TECHNICAL FIELD

The present invention relates to novel monomers each containing an electron-withdrawing group which are useful as monomers for photosensitive resins and other functional polymers and processes for producing the same, as well as to intermediates of the monomers each containing an electron-withdrawing group and processes for producing the same. In addition, it relates to polymeric compounds for use in photoresists which can be obtained from the monomers each containing an electron-withdrawing group, photosensitive resin compositions, patterning processes and processes for manufacturing semiconductors.

BACKGROUND ART

Compounds each having a bridged cyclic skeleton such as an adamantane skeleton, 3-oxatricyclo[4.3.1.1$^{4,8}$]undecane skeleton analogous to the adamantane skeleton, norbornene skeleton, 2-oxabicyclo[3.2.1$^{1,5}$]-6-octene skeleton analogous to the norbornene skeleton have three-dimensionally special ring systems. For example, these compounds are non-aromatic and rigid. These compounds can therefore exhibit various functions and receive attention in the fields of, for example, photosensitive resins in which high performances are required. Separately, a fluorine atom can impart, owing to its electric properties and other properties, special functions such as water resistance, water repellency, chemical resistance, mechanical strength, and sliding property to molecules. Investigations on organic compounds containing fluorine atoms have therefore actively been made.

However, there are known only few polymerizable compounds having higher functions, which polymerizable compounds each contain a bridged cyclic skeleton, such as the adamantane skeleton, having a polymerizable group with a fluorine atom or a group containing a fluorine atom bonded thereto and have both the functions of the bridged cyclic skeleton and the functions of the fluorine atom. In addition to these compounds, cyclic compounds each having an electron-withdrawing group such as a group containing a fluorine atom and being polymerizable have high functions and receive attention specifically in the field of photosensitive resins. Expectations with respect to novel monomers each containing an electron-withdrawing group thereby grow.

Additionally, demands have been made on polymeric compounds for use in photoresists, photosensitive resin compositions, patterning processes, and processes for manufacturing semiconductors, which can highly precisely form finer patterns.

DISCLOSURE OF INVENTION

Accordingly, an object of the present invention is to provide a novel monomer having a cyclic skeleton and containing an electron-withdrawing group and a polymerizable group, as well as to provide a process for producing the same.

Another object of the present invention is to provide a novel polymerizable bridged cyclic compound (monomer) containing a fluorine atom, which includes a bridged cyclic skeleton, such as an adamantane skeleton, and a group containing a fluorine atom bonded to the skeleton and has a polymerizable group, as well as to provide a process for producing the same.

A further object of the present invention is to provide an intermediate that is useful in production of the novel monomer having a cyclic skeleton, as well as to provide a process for producing the intermediate.

In addition, another object of the present invention is to provide a polymeric compound for use in photoresists, a photosensitive resin composition, a patterning process, and a process for manufacturing a semiconductor which can highly precisely form very fine patterns.

After intensive investigations to achieve the above objects, the present inventors have successfully synthesized novel monomers each containing an electron-withdrawing group, which include a cyclic group such as an adamantane skeleton or 3-oxatricyclo[4.3.1.1$^{4,8}$]undecane skeleton and an electron-withdrawing group, such as a group containing a fluorine atom, bonded to the cyclic group and have an ethylenic double bond. In addition, they have found that the monomers each containing an electron-withdrawing group can yield polymeric compounds for use in photoresists exhibiting high sensitivity. The present invention has been accomplished based on these findings.

Specifically, the present invention provides a monomer containing an electron-withdrawing group, represented by following Formula (a), (b) or (c):

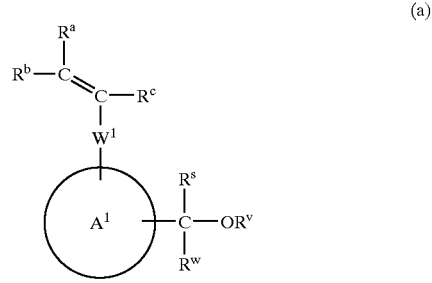

(a)

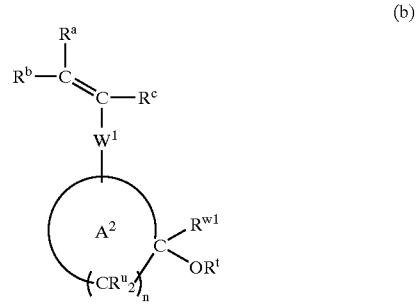

(b)

(c)

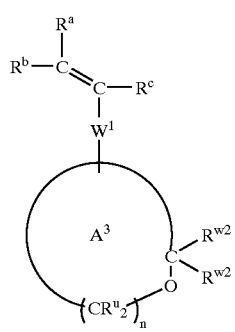

wherein $A^1$, $A^2$, and $A^3$ are each a ring; $R^a$, $R^b$, $R^c$, and $R^u$ are the same or different and are each a hydrogen atom or an organic group; at least one of $R^s$, $R^w$ and $R^v$, at least one of $R^t$ and $R^{w1}$, and at least one of the two $R^{w2}$s are each an electron-withdrawing group, and the others are each a hydrogen atom or an organic group; $W^1$ is a single bond or a linkage group; and n denotes an integer of from 2 to 25, where at least two of $R^a$, $R^b$, $R^c$, $R^s$, $R^t$, $R^u$, $R^v$, $R^w$, $R^{w1}$, $R^{w2}$, $W^1$, and carbon atoms constituting ring $A^1$, carbon atoms constituting ring $A^2$, and carbon atoms constituting ring $A^3$ may be combined to form a ring, respectively.

The electron-withdrawing groups in $R^s$, $R^t$, $R^v$, $R^w$, $R^{w1}$, and $R^{w2}$ include, for example, groups each containing a fluorine atom. Ring $A^1$, ring $A^2$ or ring $A^3$ may for example be a monocyclic ring or bridged ring containing at least a 5- to 7-membered carbocyclic ring or oxygen-containing heterocyclic ring. The monomer containing an electron-withdrawing group may have a bridged ring skeleton including ring $A^1$, ring $A^2$ or ring $A^3$ and containing 7 to 15 carbon atoms.

The present invention also provides a process for producing a monomer containing an electron-withdrawing group. The process includes the step of allowing a cyclic ketone having an ethylenic double bond, represented by following Formula (d):

(d)

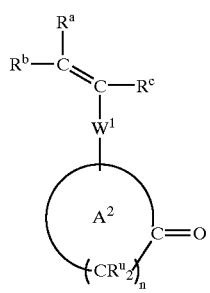

wherein $A^2$ is a ring; $R^a$, $R^b$, $R^c$ and $R^u$ are the same or different and are each a hydrogen atom or an organic group; $W^1$ is a single bond or a linkage group; and n denotes an integer of from 2 to 25, where at least two of $R^a$, $R^b$, $R^c$, $R^u$, $W^1$, and carbon atoms constituting ring $A^2$ may be combined to form a ring, respectively, to react with a fluorine reagent, or subjecting the cyclic ketone having an ethylenic double bond represented by Formula (d) to a reaction with the fluorine reagent and to a subsequent reaction for introducing a protecting group to thereby yield a monomer containing a fluorine atom and having an ethylenic double bond, represented by following Formula (b1):

(b1)

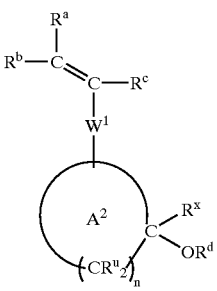

wherein $R^x$ is a group containing a fluorine atom; $R^d$ is a hydrogen atom or a hydroxyl-protecting group; $A^2$, $R^a$, $R^b$, $R^c$, $R^u$, $W^1$, and n have the same meanings as defined above, where at least two of $R^a$, $R^b$, $R^c$, $R^u$, $W^1$, and carbon atoms constituting ring A may be combined to form a ring, respectively.

The present invention further provides a process for producing a monomer containing an electron-withdrawing group. The process includes the step of allowing a cyclic thioester having an ethylenic double bond, represented by following Formula (e):

(e)

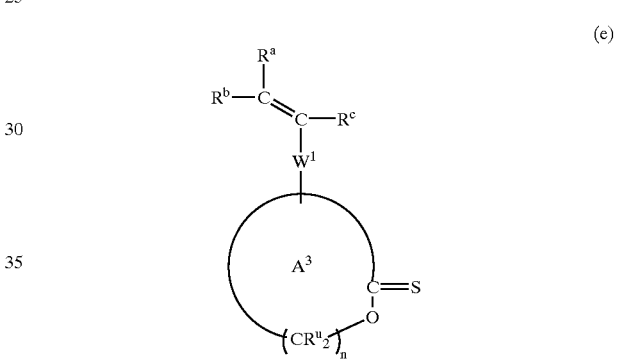

wherein $A^3$ is a ring; $R^a$, $R^b$, $R^c$, and $R^u$ are the same or different and are each a hydrogen atom or an organic group; $W^1$ is a single bond or a linkage group; and n denotes an integer of from 2 to 25, where at least two of $R^a$, $R^b$, $R^c$, $R^u$, $W^1$, and carbon atoms constituting ring $A^3$ may be combined to form a ring, respectively, to react with a fluorine reagent to thereby yield a monomer containing a fluorine atom and having an ethylenic double bond, represented by following Formula (c1):

(c1)

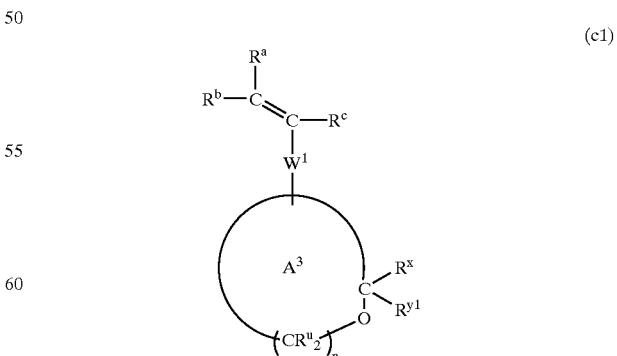

wherein $R^x$, $R^{y1}$ are each a group containing a fluorine atom; $A^3$, $R^a$, $R^b$, $R^c$, $R^u$, $W^1$, and n have the same meanings as defined above, where at least two of $R^a$, $R^b$, $R^c$, $R^u$, $W^1$, and carbon atoms constituting ring $A^3$ (maybe combined to form a ring, respectively.

In addition, the present invention provides the monomer having a cyclic thioester skeleton represented by Formula (e) The monomers each containing an electron-withdrawing group of the present invention include a compound represented by following Formula (1):

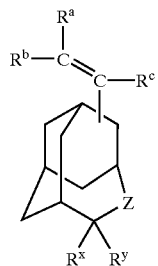

(1)

wherein $R^a$, $R^b$, and $R^c$ are the same or different and are each a hydrogen atom or an organic group, where $R^a$ and $R^b$ may be combined to form a ring with the adjacent carbon atom; Z is a single bond or an oxygen atom; $R^x$ is a group containing a fluorine atom and $R^y$ is a —$OR^d$ group, where $R^d$ is a hydrogen atom or a hydroxyl-protecting group, when Z is a single bond; $R^x$ and $R^y$ are each a group containing a fluorine atom when Z is an oxygen atom, where carbon atoms constituting the ring in the formula may each have a substituent.

The present invention also provides a process for producing a monomer containing an electron-withdrawing group. The process includes the step of allowing an adamantanone derivative having an ethylenic double bond, represented by following Formula (2):

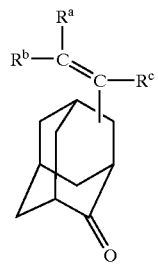

(2)

wherein $R^a$, $R^b$, and $R^c$ are the same or different and are each a hydrogen atom or an organic group, where $R^a$ and $R^b$ may be combined to form a ring with the adjacent carbon atom, and carbon atoms constituting the ring in the formula may each have a substituent, to react with a fluorine reagent, or subjecting the adamantanone derivative having an ethylenic double bond represented by Formula (2) to a reaction with a fluorine reagent and to a subsequent reaction for introducing a protecting group to thereby yield an adamantane derivative containing a fluorine atom and having an ethylenic double bond, represented by following Formula (1a):

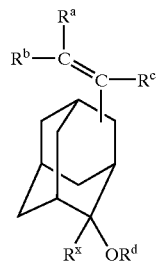

(1a)

wherein $R^a$, $R^b$, and $R^c$ have the same meanings as defined above; $R^d$ is a hydrogen atom or a hydroxyl-protecting group; and $R^x$ is a group containing a fluorine atom, where carbon atoms constituting the ring in the formula may each have a substituent.

The present invention further provides a process for producing a monomer containing an electron-withdrawing group. The process includes the step of allowing an 3-oxatricyclo[4.3.1.1$^{4,8}$]undecane-2-thione derivative having an ethylenic double bond, represented by following Formula (3a):

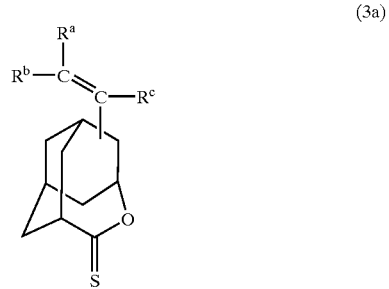

(3a)

wherein $R^a$, $R^b$, and $R^c$ are the same or different and are each a hydrogen atom or an organic group, where $R^a$ and $R^b$ may be combined to form a ring with the adjacent carbon atom, and carbon atoms constituting the ring in the formula may each have a substituent, to react with a fluorine reagent to thereby yield an 3-oxatricyclo[4.3.1.1$^{4,8}$]undecane derivative containing a fluorine atom and having an ethylenic double bond, represented by following Formula (1b):

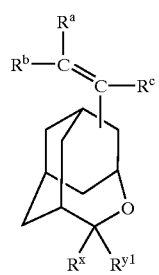

(1b)

wherein $R^a$, $R^b$, and $R^c$ have the same meanings as defined above; and $R^x$ and $R^{y1}$ are each a group containing a fluorine atom, where carbon atoms constituting the ring in the formula may each have a substituent.

The present invention also provides the adamantanone derivative having an ethylenic double bond represented by Formula (2).

The present invention further provides an 3-oxatricyclo[4.3.1.1^{4,8}]undecane derivative having an ethylenic double bond, represented by following Formula (3):

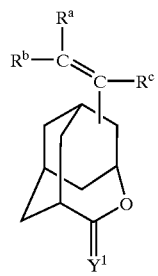

(3)

wherein $Y^1$ is an oxygen atom or a sulfur atom; and $R^a$, $R^b$, and $R^c$ are the same or different and are each a hydrogen atom or an organic group, where $R^a$ and $R^b$ may be combined to form a ring with the adjacent carbon atom, and carbon atoms constituting the ring in the formula may each have a substituent.

In addition, the present invention provides a process for producing an 3-oxatricyclo[4.3.1.1^{4,8}]undecane-2-thione derivative. The process includes the step of allowing an 3-oxatricyclo[4.3.1.1^{4,8}]undecan-2-one derivative having an ethylenic double bond, represented by following Formula (3b):

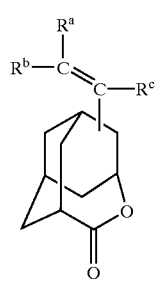

(3b)

wherein $R^a$, $R^b$, and $R^c$ are the same or different and are each a hydrogen atom or an organic group, where $R^a$ and $R^b$ may be combined to form a ring with the adjacent carbon atom, and carbon atoms constituting the ring in the formula may each have a substituent, to react with a sulfurizing agent to thereby yield the 3-oxatricyclo[4.3.1.1^{4,8}]undecane-2-thione derivative having an ethylenic double bond represented by Formula (3a).

The present invention also provides a process for producing a bridged cyclic compound having an ethylenic double bond. The process includes the step of subjecting a bridged cyclic compound containing a hydroxyalkyl group, represented by following Formula (4):

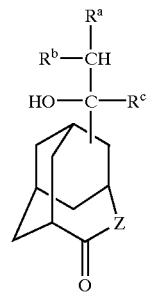

(4)

wherein $R^a$, $R^b$, and $R^c$ are the same or different and are each a hydrogen atom or an organic group, where $R^a$ and $R^b$ may be combined to form a ring with the adjacent carbon atom; and Z is a single bond or an oxygen atom, where carbon atoms constituting the ring in the formula may each have a substituent, to a dehydration reaction to thereby yield a bridged cyclic compound having an ethylenic double bond, represented by following Formula (5):

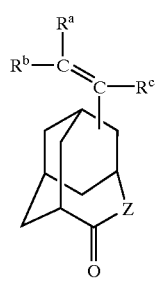

(5)

wherein $R^a$, $R^b$, and $R^c$ have the same meanings as defined above; and Z is a single bond or an oxygen atom, where carbon atoms constituting the ring in the formula may each have a substituent.

The present invention also provides the bridged cyclic compound containing a hydroxyalkyl group represented by Formula (4).

The present invention further provides a process for producing a bridged cyclic compound containing a hydroxyalkyl group. The process includes the step of subjecting a bridged cyclic compound containing an acyl group, represented by following Formula (6):

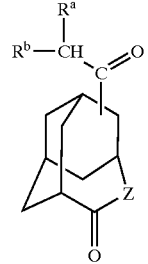

(6)

wherein $R^a$ and $R^b$ are the same or different and are each a hydrogen atom or an organic group, where $R^a$ and $R^b$ may be combined to form a ring with the adjacent carbon atom; and Z is a single bond or an oxygen atom, where carbon atoms constituting the ring in the formula may each have a substituent, to reduction or to a reaction with an organometallic compound represented by following Formula (9):

wherein $R^{c1}$ is an organic group; and M is a metallic atom which may have a ligand or a group represented by following Formula (10):

$$-MgX^1 \qquad (10)$$

wherein $X^1$ is a halogen atom,
to thereby yield the bridged cyclic compound containing a hydroxyalkyl group represented by Formula (4).

The present invention also provides the bridged cyclic compound containing an acyl group represented by Formula (6).

In addition, the present invention provides a process for producing a bridged cyclic compound containing an acyl group. The process includes the step of allowing a bridged cyclic compound represented by following Formula (7):

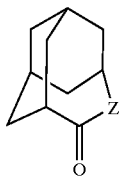

wherein Z is a single bond or an oxygen atom, and carbon atoms constituting the ring in the formula may each have a substituent, where at least one of the carbon atoms carries a hydrogen atom bonded thereto,
to react with an acylating agent comprising (A) a 1,2-dicarbonyl compound or its hydroxy reductant represented by following Formula (8):

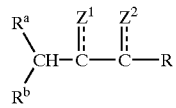

wherein $R^a$, $R^b$ and R are the same or different and are each a hydrogen atom or an organic group, where $R^a$ and $R^b$ may be combined to form a ring with the adjacent carbon atom; and $Z^1$ and $Z^2$ are the same or different and are each an oxygen atom or a hydroxyl group,
(B) oxygen, and (C) at least one compound selected from (c1) metallic compounds and (c2) N-hydroxy or N-oxo cyclic imide compounds, to thereby yield the bridged cyclic compound containing an acyl group represented by Formula (6).

The present invention further provides a process for producing a monomer containing an electron-withdrawing group. The process includes the step of allowing a cyclic compound containing an acyl group and having an ethylenic double bond, represented by following Formula (f):

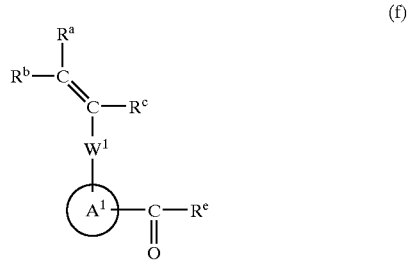

wherein $A^1$ is a ring; $R^a$, $R^b$, $R^c$, and $R^e$ are the same or different and are each a hydrogen atom or an organic group; $W^1$ is a single bond or a linkage group, where at least two of $R^a$, $R^b$, $R^c$, $R^e$, $W^1$, and carbon atoms constituting ring $A^1$ may be combined to form a ring, respectively,
to react with a fluorine reagent, or subjecting the cyclic compound containing an acyl group and having an ethylenic double bond represented by formula (f) to a reaction with the fluorine reagent and to a subsequent reaction for introducing a protecting group, to thereby yield a polymerizable cyclic compound containing a fluorine atom and having an ethylenic double bond, represented by following Formula (a1):

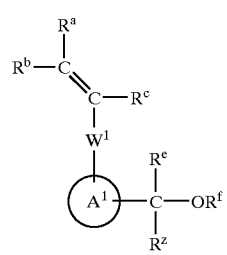

wherein $R^z$ is a group containing a fluorine atom; $R^f$ is a hydrogen atom or a hydroxyl-protecting group; and $A^1$, $R^a$, $R^b$, $R^c$, $R^e$, and $W^1$ have the same meanings as defined above, where at least two of $R^a$, $R^b$, $R^c$, $R^e$, $W^1$, and carbon atoms constituting ring $A^1$ may be combined to form a ring, respectively.

The monomers each containing an electron-withdrawing group of the present invention also include a compound represented by following Formula (12):

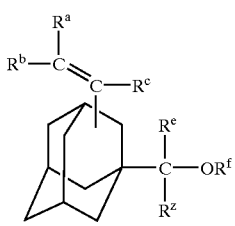

wherein $R^a$, $R^b$, $R^c$, and $R^e$ are the same or different and are each a hydrogen atom or an organic group, where $R^a$ and $R^b$ may be combined to form a ring with the adjacent carbon atom; $R^f$ is a hydrogen atom or a hydroxyl-protecting group; and $R^z$ is a group containing a fluorine atom, where carbon atoms constituting the ring in the formula may each have a substituent.

In addition, the present invention provides a process for producing a monomer containing an electron-withdrawing group. The process includes the step of allowing an acyladamantane derivative having an ethylenic double bond, represented by following Formula (13):

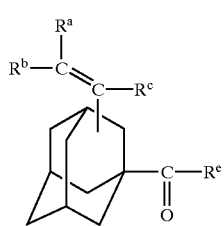

(13)

wherein $R^a$, $R^b$, $R^c$, and $R^e$ are the same or different and are each a hydrogen atom or an organic group, where $R^a$ and $R^b$ may be combined to form a ring with the adjacent carbon atom, and carbon atoms constituting the ring in the formula may each have a substituent, to react with a fluorine reagent, or subjecting the acyladamantane derivative having an ethylenic double bond represented by Formula (13) to a reaction with the fluorine reagent and to a subsequent reaction for introducing a protecting group, to thereby yield the adamantane derivative containing a fluorine atom and having an ethylenic double bond represented by Formula (12).

The present invention further provides a process for producing a bridged cyclic compound containing an acyl group. The process includes the step of allowing an adamantane derivative having an ethylenic double bond, represented by following Formula (14):

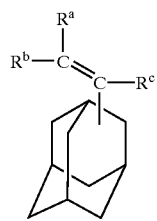

(14)

wherein $R^a$, $R^b$, and $R^c$ are the same or different and are each a hydrogen atom or an organic group, where $R^a$ and $R^b$ may be combined to form a ring with the adjacent carbon atom, and carbon atoms constituting the ring in the formula may each have a substituent, to react with an acylating agent comprising (A1) a 1,2-dicarbonyl compound or its hydroxy reductant represented by following Formula (15):

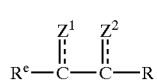

(15)

wherein $R^e$ and R are the same or different and are each a hydrogen atom or an organic group; and $Z^1$ and $Z^2$ are the same or different and are each an oxygen atom or a hydroxyl group, (B) oxygen, and (C) at least one compound selected from (c1) metallic compounds and (c2) N-hydroxy or N-oxo cyclic imide compounds, to thereby yield the acyladamantane derivative having an ethylenic double bond represented by Formula (13).

In addition, the present invention provides the acyladamantane derivative having an ethylenic double bond represented by Formula (13).

The monomers each containing an electron-withdrawing group of the present invention further include a compound represented by following Formula (16):

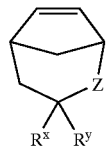

(16)

wherein Z is a single bond or an oxygen atom; $R^x$ is a group containing a fluorine atom and $R^y$ is a —$OR^d$ group, where $R^d$ is a hydrogen atom or a hydroxyl-protecting group, when Z is a single bond; and $R^x$ and $R^y$ are each a group containing a fluorine atom when Z is an oxygen atom, where carbon atoms constituting the ring in the formula may each have a substituent.

The monomers each containing an electron-with drawing group of the present invention also include a compound represented by following Formula (17):

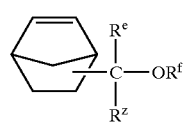

(17)

wherein $R^e$ is a hydrogen atom or an organic group; $R^f$ is a hydrogen atom or a hydroxyl-protecting group; and $R^z$ is a group containing a fluorine atom, where carbon atoms constituting the ring in the formula may each have a substituent.

In addition, the present invention provides a monomer containing an electron-withdrawing group, represented by following Formula (g), (h), (i) or (j):

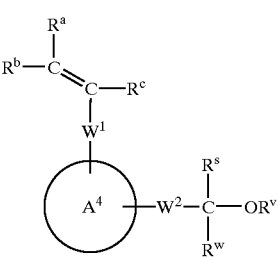

(g)

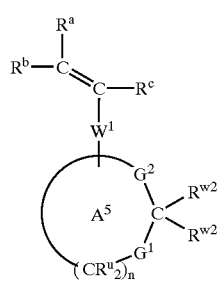

(h)

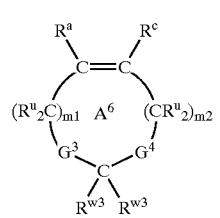

(i)

-continued

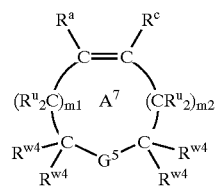
(j)

wherein $A^4$, $A^5$, $A^6$, and $A^7$ are each a ring; $R^a$, $R^b$, $R^c$, and $R^u$ are the same or different and are each a hydrogen atom or an organic group; at least one of $R^s$, $R^w$, and $R^v$ in Formula (g), at least one of the two $R^{w2}$s in Formula (h), at least one of the two $R^{w3}$s in Formula (i), and at least one of the four $R^{w4}$s in Formula (j) are each an electron-withdrawing group, and the others are each a hydrogen atom or an organic group; $W^1$ is a single bond or a linkage group; $W^2$ is a linkage group; n denotes an integer of from 2 to 25; m1 and m2 are each an integer of from 0 to 2; $G^1$, $G^3$, $G^4$, and $G^5$ are each a linkage group comprising a hetero atom; $G^2$ is a single bond or a linkage group comprising a hetero atom, where $G^2$ is a linkage group comprising a hetero atom when $G^1$ is an oxygen atom; at least two of $R^a$, $R^b$, $R^c$, $R^s$, $R^u$, $R^v$, $R^w$, $R^{w2}$, $R^{w3}$, $R^{w4}$, $W^1$, $W^2$, carbon atoms constituting ring $A^4$, carbon atoms constituting ring $A^5$, carbon atoms constituting ring $A^6$, and carbon atoms constituting ring $A^7$ may be combined to form a ring, respectively.

The electron-withdrawing groups in $R^s$, $R^v$, $R^w$, $R^{w2}$, $R^{w3}$, and $R^{w4}$ include, for example, groups each containing a fluorine atom. Ring $A^4$ or ring $A^5$ may for example be a monocyclic ring or bridged ring containing at least a 5- to 7-membered carbocyclic ring, a 5- to 7-membered oxygen-containing heterocyclic ring or a 5- to 7-membered sulfur-containing heterocyclic ring. The monomers containing an electron-withdrawing group may have a bridged cyclic skeleton including ring $A^4$ or ring $A^5$ and containing 7 to 15 carbon atoms. In the monomers containing an electron-withdrawing group, ring $A^6$ or ring $A^7$ may be a 5- or 6-membered oxygen-containing heterocyclic ring or a 5- or 6-membered sulfur-containing heterocyclic ring.

The present invention further provides a process for producing a monomer containing an electron-withdrawing group. The process includes the step of allowing a compound containing an acyl group and having an ethylenic double bond, represented by following Formula (k):

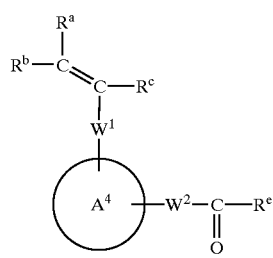
(k)

wherein $A^4$ is a ring; $R^a$, $R^b$, $R^c$, and $R^e$ are the same or different and are each a hydrogen atom or an organic group; $W^1$ is a single bond or a linkage group; $W^2$ is a linkage group, where at least two of $R^a$, $R^b$, $R^c$, $R^e$, $W^1$, $W^2$, and carbon atoms constituting ring $A^4$ may be combined to form a ring, respectively,
to react with a fluorine reagent, or subjecting the cyclic compound containing an acyl group and having an ethylenic double bond represented by Formula (k) to a reaction with the fluorine reagent and to a subsequent reaction for introducing a protecting group, to thereby yield a monomer containing a fluorine atom and having an ethylenic double bond, represented by following Formula (g1):

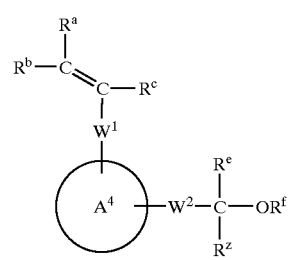
(g1)

wherein $R^z$ is a group containing a fluorine atom; $R^f$ is a hydrogen atom or a hydroxyl-protecting group; and $A^4$, $R^a$, $R^b$, $R^c$, $R^e$, $W^1$, and $W^2$ have the same meanings as defined above, where at least two of $R^a$, $R^b$, $R^c$, $R^e$, $W^1$, $W^2$, and carbon atoms constituting ring $A^4$ may be combined to form a ring, respectively.

Furthermore, the present invention provides a process for producing a monomer containing an electron-withdrawing group. The process includes the step of allowing a cyclic compound containing a hydroxyl group or a mercapto group and having an ethylenic double bond, represented by following Formula (1):

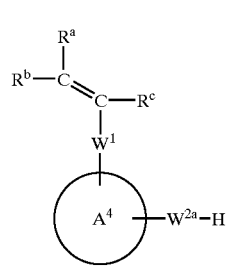
(l)

wherein $A^4$ is a ring; $R^a$, $R^b$, and $R^c$ are the same or different and are each a hydrogen atom or an organic group; $W^1$ is a single bond or a linkage group; $W^{2a}$ is an oxygen atom or a sulfur atom, where at least two of $R^a$, $R^b$, $R^c$, $W^1$, and carbon atoms constituting ring $A^4$ may be combined to form a ring, respectively, to react with a carbonyl compound containing a fluorine atom, represented by following Formula (m):

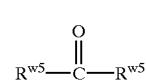
(m)

wherein $R^{w5}$ is a group containing a fluorine atom, or subjecting the cyclic compound containing a hydroxyl group or a mercapto group and having an ethylenic double bond represented by Formula (1) to a reaction with the carbonyl compound containing a fluorine atom represented by Formula (m) and to a subsequent reaction for introducing a protecting group, to thereby yield a monomer containing a fluorine atom and having an ethylenic double bond, represented by following Formula (g2):

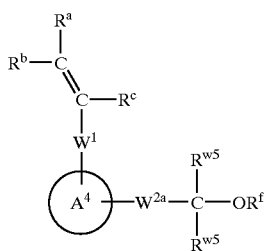

(g2)

wherein $R^f$ is a hydrogen atom or a hydroxyl-protecting group; $A^4$, $R^a$, $R^b$, $R^c$, $R^{w5}$, $W^1$, and $W^2$ have the same meanings as defined above, where at least two of $R^a$, $R^b$, $R^c$, $W^1$, and carbon atoms constituting ring $A^4$ may be combined to form a ring, respectively.

The monomers each containing an electron-withdrawing group of the present invention also include a compound represented by following Formula (18):

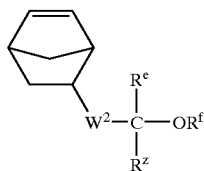

(18)

wherein $R^e$ is a hydrogen atom or an organic group; $W^2$ is a linkage group; $R^f$ is a hydrogen atom or a hydroxyl-protecting group; and $R^z$ is a group containing a fluorine atom, where carbon atoms constituting the ring in the formula may each have a substituent.

In addition, the present invention provides a process for producing a monomer containing an electron-withdrawing group. This process includes the step of allowing a cyclic compound containing a thiocarbonyl group and having an ethylenic double bond, represented by following Formula (n):

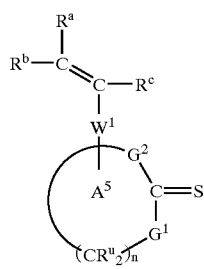

(n)

wherein $A^5$ is a ring; $R^a$, $R^b$, $R^c$, and $R^u$ are the same or different and are each a hydrogen atom or an organic group; $W^1$ is a single bond or a linkage group; n denotes an integer of from 2 to 25; $G^1$ is a linkage group comprising a hetero atom; and $G^2$ is a single bond or a linkage group comprising a hetero atom, where $G^2$ is a linkage group comprising a hetero atom when $G^1$ is an oxygen atom, and at least two of $R^a$, $R^b$, $R^c$, $R^u$, $W^1$, and carbon atoms constituting ring $A^5$ may be combined to form a ring, respectively, to react with a fluorine reagent to thereby yield a monomer containing a fluorine atom and having an ethylenic double bond, represented by following Formula (h1):

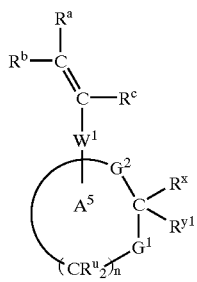

(h1)

wherein $R^x$ and $R^{y1}$ are each a group containing a fluorine atom; and $A^5$, $R^a$, $R^b$, $R^c$, $R^u$, $W^1$, n, $G^1$, and $G^2$ have the same meanings as defined above, where at least two of $R^a$, $R^b$, $R^c$, $R^u$, $W^1$, and carbon atoms constituting ring $A^5$ may be combined to form a ring, respectively.

The monomers each containing an electron-withdrawing group of the present invention further include a compound represented by following Formula (19):

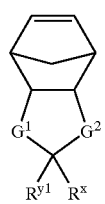

(19)

wherein $R^x$ and $R^{y1}$ are each a group containing a fluorine atom; $G^1$ is a linkage group comprising a hetero atom; and $G^2$ is a single bond or a linkage group comprising a hetero atom, where $G^2$ is a linkage group comprising a hetero atom when $G^1$ is an oxygen atom, and carbon atoms constituting the ring in the formula may each have a substituent.

The monomers each containing an electron-withdrawing group of the present invention also include a compound represented by following Formula (20):

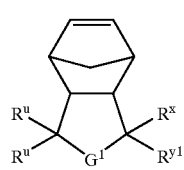

(20)

wherein $R^x$ and $R^{y1}$ are each a group containing a fluorine atom; $R^u$ is a hydrogen atom or an organic group; $G^1$ is a linkage group comprising a hetero atom, where carbon atoms constituting the ring in the formula may each have a substituent.

In addition, the present invention provides a process for producing a monomer containing an electron-withdrawing group. The process includes the step of allowing a cyclic compound containing a thiocarbonyl group and having an ethylenic double bond, represented by following Formula (o):

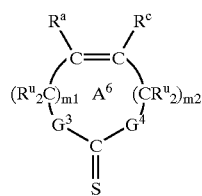

(o)

wherein $A^6$ is a ring; $R^a$, $R^c$, and $R^u$ are the same or different and are each a hydrogen atom or an organic group; m1 and m2 are each an integer of from 0 to 2; $G^3$ and $G^4$ are each a linkage group comprising a hetero atom, where at least two of $R^a$, $R^c$, $R^u$, and carbon atoms constituting ring $A^6$ may be combined to form a ring, respectively, to react with a fluorine reagent to thereby yield a monomer containing a fluorine atom and having an ethylenic double bond, represented by following Formula (i1):

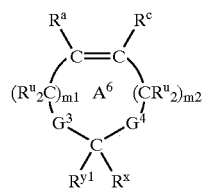

(i1)

wherein $R^x$ and $R^{y1}$ are each a group containing a fluorine atom; $A^6$, $R^a$, $R^c$, $R^u$, m1, m2, $G^3$, and $G^4$ have the same meanings as defined above, where at least two of $R^a$, $R^c$, $R^u$, and carbon atoms constituting ring $A^6$ may be combined to form a ring, respectively.

Additionally, the present invention provides a process for producing a monomer containing an electron-withdrawing group. The process includes the step of allowing a cyclic compound containing a thiocarbonyl group and having an ethylenic double bond, represented by following Formula (p):

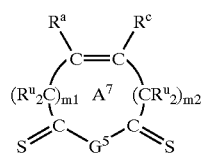

(p)

wherein $A^7$ is a ring; $R^a$, $R^c$, and $R^u$ are the same or different and are each a hydrogen atom or an organic group; m1 and m2 are each an integer of from 0 to 2; and $G^5$ is a linkage group comprising a hetero atom, where at least two of $R^a$, $R^c$, $R^u$, and carbon atoms constituting ring $A^7$ may be combined to form a ring, respectively, to react with a fluorine reagent to thereby yield a monomer containing a fluorine atom and having an ethylenic double bond, represented by following Formula (j1):

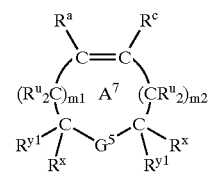

(j1)

wherein $R^x$ and $R^{y1}$ are each a group containing a fluorine atom; and $A^7$, $R^a$, $R^c$, $R^u$, m1, m2, and $G^5$ have the same meanings as defined above, where at least two of $R^a$, $R^c$, $R^u$, and carbon atoms constituting ring $A^7$ may be combined to form a ring, respectively.

The monomers each containing an electron-withdrawing group of the present invention also include a compound represented by following Formula (21):

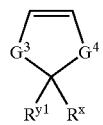

(21)

wherein $R^x$ and $R^{y1}$ are each a group containing a fluorine atom; and $G^3$ and $G^4$ are each a linkage group comprising a hetero atom, where carbon atoms constituting the ring in the formula may each have a substituent.

The monomers each containing an electron-withdrawing group of the present invention also include a compound represented by following Formula (22):

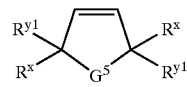

(22)

wherein $R^x$ and $R^{y1}$ are each a group containing a fluorine atom; and $G^5$ is a linkage group comprising a hetero atom, where carbon atoms constituting the ring in the formula may each have a substituent.

In addition, the present invention provides a polymeric compound for use in photoresists. The polymeric compound includes at least one of constitutional repeating units represented by following Formula (G), (H), (I), or (J):

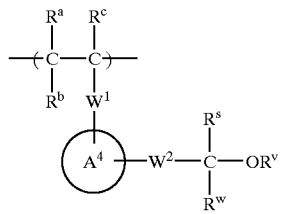

(G)

-continued

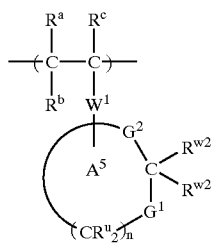

(H)

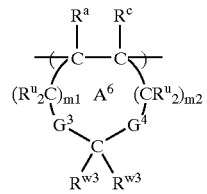

(I)

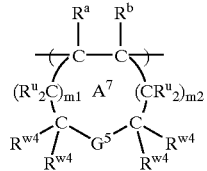

(J)

wherein $A^4$, $A^5$, $A^6$, and $A^7$ are each a ring; $R^a$, $R^b$, $R^c$, and $R^u$ are the same or different and are each a hydrogen atom or an organic group; at least one of $R^s$, $R^w$, and $R^v$ in Formula (G), at least one of the two $R^{w2}$s in Formula (H), at least one of the two $R^{w3}$s in Formula (I), and at least one of the four $R^{w4}$s in Formula (J) are each an electron-withdrawing group, and the others are each a hydrogen atom or an organic group; $W^1$ is a single bond or a linkage group; $W^2$ is a linkage group; n denotes an integer of from 2 to 25; m1 and m2 are each an integer of from 0 to 2; $G^1$, $G^3$, $G^4$, and $G^5$ are each a linkage group comprising a hetero atom; $G^2$ is a single bond or a linkage group comprising a hetero atom, where $G^2$ is a linkage group comprising a hetero atom when $G^1$ is an oxygen atom; at least two of $R^a$, $R^b$, $R^c$, $R^s$, $R^u$, $R^v$, $R^w$, $R^{w2}$, $R^{w3}$, $R^{w4}$, $W^1$, $W^2$ carbon atoms constituting ring $A^4$, carbon atoms constituting ring $A^5$, carbon atoms constituting ring $A^6$, and carbon atoms constituting ring $A^7$ may be combined to form a ring, respectively.

The present invention further provides a photosensitive resin composition including at least the polymeric compound for use in photoresists and a photosensitive acid generator.

In addition, the present invention provides a patterning process including at least the steps of applying the photosensitive resin composition to a substrate, applying light with a wavelength of less than or equal to 220 nm, baking, and developing. As the light for use herein, $F_2$ excimer laser light can be used.

In addition and advantageously, the present invention provides a process for manufacturing a semiconductor. The process includes the step of patterning according to the aforementioned patterning process.

In the present description, the term "monomer" means a starting substance which is used in the formation of a polymer by polymerization reaction and is a constitutional unit compound of the polymer. The term "organic group" is used in a broad meaning including groups containing non-metallic atoms, such as halogen atoms, hydroxyl group, mercapto group, amino group, nitro group, and sulfonic acid groups, in addition to groups containing carbon atoms. The term "group containing a fluorine atom" also includes a fluorine atom. The "hydroxyl-protecting group" in, for example, $R^d$ means a functional group that can be derived from a hydroxyl group and also includes groups that are hardly deprotected, in addition to groups that can easily be deprotected. The term "fluorine reagent" means a reagent that can introduce not only a fluorine atom but also a group containing a fluorine atom in a broad meaning, such as trifluoromethyl group.

BEST MODE FOR CARRYING OUT THE INVENTION

[Monomers Containing an Electron-withdrawing Group]

The monomers each containing an electron-withdrawing group of the present invention are represented by Formula (a), (b) or (c). They also include the monomers represented by Formula (g), (h), (i) or (j).

In the monomers (polymerizable cyclic compounds) each containing an electron-withdrawing group represented by Formula (a), ring $A^1$ is preferably a non-aromatic carbocyclic ring or heterocyclic ring, of which a non-aromatic carbocyclic ring and a non-aromatic oxygen-atom-containing heterocyclic ring are typically preferred. Such non-aromatic carbocyclic rings include, but are not limited to, cyclopentane ring, cyclohexane ring, cyclohexene ring, cycloheptane ring, cyclooctane ring, cyclodecane ring, cyclododecane ring, and other monocyclic rings; adamantane ring, norbornane ring, norbornene ring, decalin ring, perhydroindene ring, perhydrofluorene ring, perhydroanthracene ring, tricyclo[5.2.1.0$^{2,6}$]decane ring, tetracyclo[4.4.0.1$^{2,5}$.1$^{7,10}$]dodecane ring, and other bridged rings. Such non-aromatic oxygen-atom-containing heterocyclic rings include, but are not limited to, 3-oxatricyclo[4.3.1.1$^{4,8}$]undecane ring, 2-oxabicyclo[3.2.1$^{1,5}$]octane ring, 3-oxabicyclo[3.2.1$^{1,5}$]octane ring, 2-oxabicyclo[2.2.2$^{1,4}$]]octane ring, and 6-oxatricyclo[3.2.1.1$^{3,8}$]nonane ring. Ring $A^1$ may have a substituent. Such substituents include similar groups to substituents which the undermentioned organic groups or hydrocarbon groups may have.

$R^a$, $R^b$, and $R^c$ are the same or different and are each a hydrogen atom or an organic group. Such organic groups are not specifically limited and include, for example, hydrocarbon groups, heterocyclic groups, halogen atoms, alkoxycarbonyl groups, aryloxycarbonyl groups, acyl groups, cyano group, and nitro group.

The hydrocarbon groups include aliphatic hydrocarbon groups, alicyclic hydrocarbon group, and aromatic hydrocarbon groups. Such aliphatic hydrocarbon groups include, but are not limited to, methyl, ethyl, propyl, isopropyl, butyl, isobutyl, s-butyl, t-butyl, pentyl, hexyl, octyl, decyl, tetradecyl, hexadecyl, octadecyl, allyl, and other straight- or branched-chain aliphatic hydrocarbon groups (alkyl groups, alkenyl groups, and alkynyl groups) each containing from about 1 to about 20 carbon atoms. Among them, those having from about 1 to about 10 carbon atoms are preferred, of which those having from about 1 to about 6 carbon atoms are typically preferred. The alicyclic hydrocarbon groups include, but are not limited to, cyclopropyl, cyclobutyl, cyclopentyl, cyclohexyl, cyclohexenyl, cyclooctyl, cyclodecyl, cyclododecyl, and other alicyclic hydrocarbon groups (e.g., cycloalkyl groups and cycloalkenyl groups) each containing from about 3 to about 20 carbon atoms, of which those containing from about 3 to about 15 carbon atoms are preferred. The aromatic hydrocarbon groups include, but are not limited to, phenyl, naphthyl, and other aromatic hydrocarbon groups each containing from about 6 to about 14 carbon atoms.

These hydrocarbon groups may have substituents. Such substituents include, but are not limited to, halogen atoms (fluorine, chlorine, bromine, and iodine atoms), oxo group, hydroxyl group which may be protected by a protecting group, hydroxymethyl group which may be protected by a protecting group, amino group which may be protected by a protecting group, carboxyl group which may be protected by a protecting group, substituted oxycarbonyl groups, substituted or unsubstituted carbamoyl groups, nitro group, acyl groups, cyano group, alkyl groups (e.g., methyl, ethyl, and other $C_1$–$C_4$ alkyl groups), cycloalkyl groups, aryl groups (e.g., phenyl and naphthyl groups), and heterocyclic groups. As the protecting groups, conventional protecting groups in the field of organic synthesis can be used. Typical examples of hydrocarbon groups each having a substituent are chloromethyl group, trifluoromethyl group, and other halogenated hydrocarbon groups.

Heterocyclic rings constituting the heterocyclic groups include aromatic heterocyclic rings and non-aromatic heterocyclic rings. Such heterocyclic rings include, but are not limited to, heterocyclic rings each containing an oxygen atom as a hetero atom (e.g., furan, tetrahydrofuran, oxazole, isoxazole, and other 5-membered rings, 4-oxo-4H-pyran, tetrahydropyran, morpholine, and other 6-membered rings, benzofuran, isobenzofuran, 4-oxo-4H-chromene, chroman, isochroman, and other condensed rings), heterocyclic rings each containing a sulfur atom as a hetero atom (e.g., thiophene, thiazole, isothiazole, thiadiazole, and other 5-membered rings, 4-oxo-4H-thiopyran and other 6-membered rings, benzothiophene and other condensed rings), heterocyclic rings each containing a nitrogen atom as a hetero atom (e.g., pyrrole, pyrrolidine, pyrazole, imidazole, triazole, and other 5-membered rings, pyridine, pyridazine, pyrimidine, pyrazine, piperidine, piperazine, and other 6-membered rings, indole, indoline, quinoline, acridine, naphthyridine, quinazoline, purine, and other condensed rings). These heterocyclic groups may have substituents such as the substituents which the hydrocarbon groups may have.

The halogen atoms include fluorine, chlorine, bromine, and iodine atoms. The alkoxycarbonyl groups include, but are not limited to, methoxycarbonyl group and ethoxy carbonyl group. The aryloxycarbonyl groups include, for example, phenyloxycarbonyl group. The acyl groups include, but are not limited to, formyl group, acetyl group, propionyl group, and benzoyl group.

Preferred $R^a$, $R^b$, and $R^c$ include, for example, hydrogen atom; methyl, ethyl, propyl, isopropyl, butyl, and other $C_1$–$C_{10}$ aliphatic hydrocarbon groups (specifically, $C_1$–$C_4$ alkyl groups); alicyclic hydrocarbon groups (especially, $C_3$–$C_{15}$ cycloalkyl groups or cycloalkenyl groups); $C_6$–$C_{14}$ aryl groups; trifluoromethyl group and other halogenated hydrocarbon groups; fluorine atom, chlorine atom, and other halogen atoms.

At least one of $R^s$, $R^w$ and $R^v$, at least one of $R^t$ and $R^{w1}$, and at least one of the two $R^{w2}$s are each an electron-withdrawing group, and the others are each a hydrogen atom or an organic group.

Such electron-withdrawing groups include, but are not limited to, fluorine atom and other halogen atoms, trifluoromethyl group and other halogenated hydrocarbon groups, methoxycarbonyl group and other alkoxycarbonyl groups, phenoxycarbonyl group and other aryloxycarbonyl groups, acetyl group and other acyl groups, cyano group, aryl groups, and 1-alkenyl groups. Among them, fluorine atom, trifluoromethyl group and other groups each containing a fluorine atom are preferred. The organic groups include those similar to the organic groups in $R^a$, $R^b$, and $R^c$. Preferably, $R^s$ and $R^w$ are both electron-withdrawing groups. The group $R^v$ may be a hydroxyl-protecting group as in $R^d$ mentioned later.

$W^1$ is a single bond or a linkage group. Such linkage groups include, but are not limited to, methylene group, ethylene group, and other alkylene groups; alkenylene groups; phenylene group and other arylene groups; ester bond (—C(=O)—O—); ketone group (—C(=O)—); oxygen atom (ether bond); sulfur atom (thioether bond); and divalent groups each comprising a plurality of these groups bonded with each other. $W^1$ may be a single bond or an ester bond in many cases and is typically preferably a single bond.

At least two of $R^a$, $R^b$, $R^c$, $R^s$, $R^v$, $R^w$, $W^1$, and carbon atoms constituting ring $A^1$ may be combined to form a ring, respectively. Such rings include, but are not limited to, cyclopropane, cyclobutane, cyclopentane, cyclopentene, cyclohexane, cyclohexene, cyclooctane, cyclodecane, cyclododecane ring, decalin ring, adamantane ring, norbornane ring, norbornene ring, and other non-aromatic carbocyclic rings (cycloalkane rings, cycloalkene rings, and bridged carbocyclic rings) each containing from about 3 to about 20 members, preferably from about 3 to about 15 members, more preferably from about 5 to about 15 members, and typically from about 5 to about 8 members; and non-aromatic oxygen-atom-containing heterocyclic rings. These rings may have substituents such as the substituents which the hydrocarbon groups may have and may carry another ring (a non-aromatic ring or an aromatic ring) condensed thereto.

When a carbon atom constituting ring $A^1$ is combined with $R^a$, $R^b$, $R^c$, $R^s$, $R^v$, $R^w$, or $W^1$, a condense ring is formed. Such condensed rings include the bridged rings such as adamantane ring, norbornane ring, norbornene ring, and other bridged carbocyclic rings; 3-oxatricyclo[4.3.1.1$^{4,8}$]undecane ring, 2-oxabicyclo[3.2.1$^{1,5}$]octane ring, 3-oxabicyclo[3.2.1$^{1,5}$]octane ring, 2-oxabicyclo[2.2.2$^{1,4}$]]octane ring, 6-oxatricyclo[3.2.1.1$^{3,8}$]nonane ring, and other oxygen-atom-containing bridged heterocyclic rings.

The position on ring $A^1$ at which $W^1$ is combined is not specifically limited, but is often a bridgehead position when ring $A^1$ forms a bridged ring.

Typical examples of the monomers each containing an electron-withdrawing group represented by Formula (a) are the compounds represented by Formula (a1), such as the polymerizable adamantane derivatives each containing a fluorine atom represented by Formula (12), and the norbornene derivatives each containing a fluorine atom represented by Formula (17).

In the monomers (polymerizable cyclic compounds) each containing an electron-withdrawing group represented by Formula (b), ring $A^2$ includes non-aromatic carbocyclic rings such as cyclopentane ring, cyclohexane ring, cycloheptane ring, cyclooctane ring, cyclodecane ring, and cyclododecane ring. The repetition number n is an integer of from 2 to 25, preferably an integer of from 4 to 19, and more preferably an integer of from 4 to 14. Ring $A^2$ may have a substituent. Such substituents include groups similar to the substituents which the organic groups and the hydrocarbon groups may have.

$R^a$, $R^b$, $R^c$, and $R^u$ are the same or different and are each a hydrogen atom or an organic group. The plural $R^u$s may be the same or different. The organic group includes similar groups as above.

Preferred $R^a$, $R^b$, $R^c$, and $R^u$ include hydrogen atom; methyl, ethyl, propyl, isopropyl, butyl, and other $C_1$–$C_{10}$ aliphatic hydrocarbon groups (specifically, $C_1$–$C_4$ alkyl groups); alicyclic hydrocarbon groups (specifically, $C_3$–$C_{15}$ cycloalkyl groups or cycloalkenyl groups); $C_6$–$C_{14}$ aryl groups; trifluoromethyl group and other halogenated hydrocarbon groups; fluorine atom, chlorine atom, and other halogen atoms. $R^t$ may be a hydroxyl-protecting group as in $R^f$ mentioned later.

The electron-withdrawing groups and organic groups in $R^{w1}$ and $R^t$ include similar groups to the electron-withdrawing groups and organic groups in, for example, $R^s$. $R^{w1}$ is preferably an electron-withdrawing group, of which fluorine atom, trifluoromethyl group and other groups each containing a fluorine atom are typically preferred. $W^1$ has the same meaning as in Formula (a).

At least two of $R^a$, $R^b$, $R^c$, $R^t$, $R^u$, $R^{w1}$, $W^1$, and carbon atoms constituting ring $A^2$ may be combined to form a ring, respectively. Such rings include, for example, similar rings to those formed by at least two of, for example, $R^a$ and $R^b$ in the compounds represented by Formula (a).

When a carbon atom constituting ring $A^2$ is combined with $R^a$, $R^b$, $R^c$, $R^t$, $R^u$, $R^{w1}$, or $W^1$, a condensed ring is formed. Such condensed rings include the bridged rings such as adamantane ring, norbornane ring, norbornene ring, and other bridged carbocyclic rings; 3-oxatricyclo[4.3.1.1$^{4,8}$]undecane ring, 2-oxabicyclo[3.2.1$^{1,5}$]octane ring, 3-oxabicyclo[3.2.1$^{1,5}$]octane ring, 2-oxabicyclo[2.2.2$^{1,4}$]octane ring, 6-oxatricyclo[3.2.1.1$^{3,8}$]nonane ring, and other oxygen-atom-containing bridged heterocyclic rings.

The position on ring $A^2$ at which $W^1$ is combined is not specifically limited, but is often a bridgehead position when ring $A^2$ forms a bridged ring.

Typical examples of the monomers each containing an electron-withdrawing group represented by Formula (b) include the compounds represented by Formula (b1) such as the polymerizable adamantane derivatives each containing a fluorine atom represented by Formula (1a), and norbornene derivatives each containing a fluorine atom. Such norbornene derivatives are compounds represented by Formula (16) in which Z is a single bond and $R^y$ is a —$OR^d$.

In the monomers (polymerizable cyclic compounds) each containing an electron-withdrawing group represented by Formula (c), ring $A^3$ includes, for example, non-aromatic oxygen-atom-containing heterocyclic rings such as oxane ring, oxepane ring, oxocane ring, oxonane ring, oxecane ring, and other non-aromatic oxygen-atom-containing heterocyclic rings each containing from about 6 to about 21 members. The repetition number n is an integer of from 2 to 25, preferably an integer of from 4 to 19, and more preferably an integer of from 4 to 14. Ring $A^3$ may have a substituent. Such substituents include groups similar to the substituents which the organic groups and the hydrocarbon groups may have.

$R^a$, $R^b$, $R^c$, and $R^u$ are the same or different and are each a hydrogen atom or an organic group. The plural $R^u$s may be the same or different. The organic group includes similar groups as above.

Preferred $R^a$, $R^b$, $R^c$, and $R^u$ include hydrogen atom; methyl, ethyl, propyl, isopropyl, butyl, and other $C_1$–$C_{10}$ aliphatic hydrocarbon groups (specifically, $C_1$–$C_4$ alkyl groups); alicyclic hydrocarbon groups (specifically, $C_3$–$C_{15}$ cycloalkyl groups or cycloalkenyl groups); $C_6$–$C_{14}$ aryl groups; trifluoromethyl group and other halogenated hydrocarbon groups; fluorine atom, chlorine atom, and other halogen atoms.

The two $R^{w2}$s are both electron-withdrawing groups or one is an electron-withdrawing group and the other is a hydrogen atom or an organic group. Such electron-withdrawing groups and organic groups are similar to those mentioned above. Preferably, the two $R^{w2}$s are both electron-withdrawing groups. In this case, the two electron-withdrawing groups as $R^{w2}$s may be the same or different. As the electron-withdrawing groups, fluorine atom, trifluoromethyl group, and other groups containing a fluorine atom are preferred. $W^1$ has the same meaning as in Formula (a).

At least two of $R^a$, $R^b$, $R^c$, $R^u$, $R^{w2}$, $W^1$, and carbon atoms constituting ring $A^3$ may be combined to form a ring, respectively. Such rings include, for example, similar rings to those formed by at least two of, for example, $R^a$ and $R^b$ in the compounds represented by Formula (a).

When a carbon atom constituting ring $A^3$ is combined with $R^a$, $R^b$, $R^c$, $R^u$, $R^{w2}$, or $W^1$, a condensed ring is formed. Such condensed rings include, for example, 3-oxatricyclo[4.3.1.1$^{4,8}$]undecane ring, 2-oxabicyclo[3.2.1$^{1,5}$]octane ring, 3-oxabicyclo[3.2.1$^{1,5}$]octane ring, 2-oxabicyclo[2.2.2$^{1,4}$]octane ring, 6-oxatricyclo[3.2.1.1$^{3,8}$]nonane ring, and other oxygen-atom-containing bridged heterocyclic rings.

The position on ring $A^3$ at which $W^1$ is combined is not specifically limited, but is often a bridgehead position when ring $A^3$ forms a bridged ring.

Typical examples of the monomers each containing an electron-withdrawing group represented by Formula (c) include the compounds represented by Formula (c1) such as the polymerizable 3-oxatricyclo[4.3.1.1$^{4,8}$]undecane derivatives each containing a fluorine atom represented by Formula (1b), and polymerizable 2-oxabicyclo[3.2.1$^{1,5}$]octane derivatives. The polymerizable 2-oxabicyclo[3.2.1$^{1,5}$]octane derivatives each containing a fluorine atom are compounds represented by Formula (16) in which Z is an oxygen atom and $R^x$ and $R^y$ are groups each containing a fluorine atom.

In the monomers (polymerizable cyclic compounds) each having an electron-withdrawing group represented by Formula (g), ring $A^4$ is similar to ring $A^1$ in Formula (a), and $R^a$, $R^b$, $R^c$, $R^s$, $R^w$, $R^v$, and $W^1$ are similar to those in Formula (a). The linkage group in $W^2$ includes, but is not limited to, methylene group, ethylene group, and other alkylene groups; alkenylene groups; phenylene group and other arylene groups; ester bond (—C(=O)—O—); ketone group (—C(=O)—); oxygen atom (ether bond); sulfur atom (thioether bond); —NH—; and divalent groups comprising a plurality of these groups bonded with each other. The linkage groups may each have a substituent. $W^2$ is often an ester bond (—C(=O)—O—); ketone group (—C(=O)—); oxygen atom (ether bond); sulfur atom (thioether bond); —NH—; or —$CH_2$—O—.

At least two of $R^a$, $R^b$, $R^c$, $R^s$, $R^v$, $R^w$, $W^1$, $W^2$, and carbon atoms constituting ring $A^4$ may be combined to form a ring, respectively. Such rings include, for example, similar rings to those formed by at least two of $R^a$, $R^b$, $R^c$, $R^s$, $R^v$, $R^w$, $W^1$, and carbon atoms constituting ring $A^1$ in the compounds represented by Formula (a).

When a carbon atom constituting ring $A^4$ is combined with $R^a$, $R^b$, $R^c$, $R^s$, $R^v$, $R^w$, $W^1$ or $W^2$, a condensed ring is formed. Such condensed rings include the bridged rings such as adamantane ring, norbornane ring, norbornene ring, and other bridged carbocyclic rings; 3-oxatricyclo[4.3.1.1$^{4,8}$]undecane ring, 2-oxabicyclo[3.2.1$^{1,5}$]octane ring, 3-oxabicyclo[3.2.1$^{1,5}$]octane ring, 2-oxabicyclo[2.2.2$^{1,4}$]octane ring, 6-oxatricyclo[3.2.1.1$^{3,8}$]nonane ring, and other oxygen-atom-containing bridged heterocyclic rings.

The position on ring $A^4$ at which $W^1$ is combined is not specifically limited, but is often a bridgehead position when ring $A^4$ is a bridged ring. The position on ring $A^4$ at which $W^2$ is combined is not specifically limited.

Typical examples of the monomers each containing an electron-withdrawing group represented by Formula (g) include the compounds represented by Formulae (g1) and (g2), such as the norbornene derivatives each containing a fluorine atom represented by Formula (18).

In the monomers (polymerizable cyclic compounds) each containing an electron-withdrawing group represented by Formula (h), ring $A^5$ is similar to ring $A^3$ in Formula (c), and $R^a$, $R^b$, $R^c$, $R^u$, $R^{w2}$, $W^1$, and n are similar to those in Formula (c). $G^1$ is a linkage group comprising a hetero atom, and $G^2$ is a single bond or a linkage group comprising a hetero atom. When $G^1$ is an oxygen atom, $G^2$ is a linkage group comprising a hetero atom.

Such linkage groups each comprising a hetero atom may be divalent groups each comprising at least one (for example, one to three) hetero atom in a principle chain. Such groups include, for example, oxygen atom (ether bond), sulfur atom (thioether bond), —S(=O)—O—, —S(=O)$_2$—O—, —NH—, silicon atom (—Si—), and —OP(=O) —O—. Among them, oxygen atom (ether bond), sulfur atom (thioether bond), —S(=O)—O—, and —S(=O)$_2$—O— are preferred.

At least two of $R^a$, $R^b$, $R^c$, $R^u$, $R^{w2}$, $W^1$, and carbon atoms constituting ring $A^5$ may be combined to form a ring, respectively. Such rings include, for example, similar rings to those formed by at least two of $R^a$, $R^b$, $R^c$, $R^s$, $R^v$, $R^w$, $W^1$, and carbon atoms constituting ring $A^1$ in the compounds represented by Formula (a).

When a carbon atom constituting ring $A^5$ is combined with $R^a$, $R^b$, $R^c$, $R^u$, $R^{w2}$ or $W^1$, a condensed ring is formed. Such condensed rings include the bridged rings such as adamantane ring, norbornane ring, norbornene ring, and other bridged carbocyclic rings; 3-thiatricyclo[4.3.1.1$^{4,8}$] undecane ring, 2-thiabicyclo[3.2.1$^{1,5}$]octane ring, 3-thiabicyclo[3.2.1$^{1,5}$]octane ring, 2-thiabicyclo[2.2.2$^{1,4}$]] octane ring, 6-thiatricyclo[3.2.1.1$^{3,8}$]nonane ring, and other sulfur-atom-containing bridged heterocyclic rings.

The position on ring $A^5$ at which $W^1$ is combined is not specifically limited, but is often a bridgehead position when ring $A^5$ is a bridged ring.

Typical examples of the monomers each containing an electron-withdrawing group represented by Formula (h) include the compounds represented by Formula (h), such as the norbornene derivatives each containing an electron-withdrawing group represented by Formula (19) or (20).

In the monomers (polymerizable cyclic compounds) each containing an electron-withdrawing group represented by Formula (i), $A^6$ is preferably a non-aromatic heterocyclic ring such as dioxolene ring and dithiolene ring. $R^a$, $R^c$, and $R^u$ are similar to those in Formula (c). The organic group and electron-withdrawing group in $R^{w3}$ are similar to those in $R^{w2}$ in Formula (c). The repetition numbers m1 and m2 are each an integer of from 0 to 2. The linkage groups comprising a hetero atom in $G^3$ and $G^4$ include similar groups to those in $G^1$. Among them, oxygen atom (ether bond), sulfur atom (thioether bond), —S(=O)—O—, and —S(=O)$_2$—O— are preferred.

At least two of $R^a$, $R^c$, $R^u$, $R^{w3}$, and carbon atoms constituting ring $A^6$ may be combined to form a ring, respectively. Such rings include, for example, similar rings to those formed by at least two of $R^a$, $R^b$, $R^c$, $R^s$, $R^v$, $R^w$, $W^1$, and carbon atoms constituting ring $A^1$ in Formula (a).

Typical examples of the monomers each containing an electron-withdrawing group represented by Formula (i) include the compounds represented by Formula (i1), such as the heterocyclic compounds each containing an electron-withdrawing group represented by Formula (21).

In the monomers (polymerizable cyclic compounds) each containing an electron-withdrawing group represented by Formula (j), $A^7$ is preferably a non-aromatic heterocyclic ring such as oxolene ring and thiolene ring. $R^a$, $R^c$, and $R^u$ are similar to those in Formula (c). The organic group and electron-withdrawing group in $R^{w4}$ are similar to those in $R^{w2}$ in Formula (c). The repetition numbers m1 and m2 are each an integer of from 0 to 2. The linkage group comprising a hetero atom in $G^5$ includes similar groups to those in $G^1$. Among them, oxygen atom (ether bond), sulfur atom (thioether bond), —S(=O)—O—, and —S(=O)$_2$—O— are preferred.

At least two of $R^a$, $R^c$, $R^u$, $R^{w4}$, and carbon atoms constituting ring $A^7$ may be combined to form a ring, respectively. Such rings include, for example, similar rings to those formed by at least two of $R^a$, $R^b$, $R^c$, $R^s$, $R^v$, $R^w$, $W^1$, and carbon atoms constituting ring $A^1$ in Formula (a).

Typical examples of the monomers each containing an electron-withdrawing group represented by Formula (j) include the compounds represented by Formula (j1), such as the heterocyclic compounds containing an electron-withdrawing group represented by Formula (22).

In the monomers containing an electron-withdrawing group of the present invention, the electron-withdrawing groups in $R^s$, $R^v$, $R^w$, $R^t$, $R^{w1}$, $R^{w2}$, $R^{w3}$ and $R^{w4}$ are specifically preferably groups each containing a fluorine atom. Ring $A^1$, ring $A^2$, ring $A^3$, ring $A^4$ or ring $A^5$ is preferably a monocyclic ring or bridged ring containing at least a 5- to 7-membered carbocyclic ring or oxygen-containing heterocyclic ring. Preferred monomers containing an electron-withdrawing group have a bridged cyclic skeleton including ring $A^1$, ring $A^2$, ring $A^3$, ring $A^4$ or ring $A^5$ and containing from 7 to 15 carbon atoms. Ring $A^6$ and ring $A^7$ are preferably 5- or 6-membered oxygen-containing heterocyclic rings or 5- or 6-membered sulfur-containing heterocyclic rings.

[Compounds Represented by Formula (b1) and Production Thereof]

The compounds represented by Formula (b1) correspond to compounds represented by Formula (b) in which $R^{w1}$ is a group containing a fluorine atom; and $R^t$ is a hydrogen atom or a hydroxyl-protecting group.

In Formula (b1), the group containing a fluorine atom in $R^x$ includes, for example, fluorine atom and trifluoromethyl group. The hydroxyl-protecting group in $R^d$ includes, but is not limited to, alkyl groups (e.g., methyl, t-butyl, and other $C_1$–$C_4$ alkyl groups), alkenyl groups (e.g., allyl group), cycloalkyl groups (e.g., cyclohexyl group), aryl groups (e.g., 2,4-dinitrophenyl group), aralkyl groups (e.g., benzyl, 2,6-dichlorobenzyl, 3-bromobenzyl, 2-nitrobenzyl, and triphenylmethyl groups); substituted methyl groups (e.g., methoxymethyl, methylthiomethyl, benzyloxymethyl, t-butoxymethyl, 2-methoxyethoxymethyl, 2,2,2-trichloroethoxymethyl, bis(2-chloroethoxy)methyl, and 2-(trimethylsilyl)ethoxymethyl groups), substituted ethyl groups (e.g., 1-ethoxyethyl, 1-methyl-1-methoxyethyl, 1-isopropoxyethyl, and 2,2,2-trichloroethyl groups), tetrahydropyranyl group, tetrahydrofuranyl group, 1-hydroxyalkyl groups (e.g., 1-hydroxyethyl, 1-hydroxyhexyl, 1-hydroxydecyl, and 1-hydroxyhexadecyl groups), and other groups that can form an acetal or hemiacetal group with a hydroxyl group; acyl groups (e.g., formyl, acetyl, propionyl, butyryl, isobutyryl, valeryl, pivaloyl, and other $C_1$–$C_6$ aliphatic acyl groups; acetoacetyl group; benzoyl, naphthoyl, and other aromatic acyl groups), alkoxycarbonyl groups (e.g., methoxycarbonyl, ethoxycarbonyl, t-butoxycarbonyl, and other $C_1$–$C_4$ alkoxycarbonyl groups), aralkyloxycarbonyl groups (e.g., benzyloxycarbonyl group and p-methoxybenzyloxycarbonyl group), substituted or unsubstituted carbamoyl groups (e.g., carbamoyl, methylcarbamoyl, and phenylcarbamoyl groups), dialkylphosphinothioyl groups, diarylphosphinothioyl groups, substituted silyl groups (e.g., trimethylsilyl, t-butyldimethylsilyl, tribenzylsilyl, and triphenylsilyl groups), and groups each containing a fluorine atom (e.g., trifluoromethyl group). Preferred hydroxyl-protecting groups include $C_1$–$C_4$ alkyl groups; substituted methyl groups, substituted ethyl groups, 1-hydroxyalkyl groups, and other groups that can form an acetal or hemiacetal group with a hydroxyl group; acyl groups, $C_1$–$C_4$ alkoxy-carbonyl groups, substituted or unsubstituted carbamoyl groups, and substituted silyl groups.

Each of the monomers containing a fluorine atom and having an ethylenic double bond represented by Formula (b1) can be produced by allowing the cyclic ketone having an ethylenic double bond represented by Formula (d) to react with a fluorine reagent or subjecting the cyclic ketone having an ethylenic double bond represented by Formula (d) to a reaction with a fluorine reagent and to a subsequent reaction for introducing a protecting group.

The symbols in Formula (d) have the same meanings as above. The fluorine reagent is not specifically limited as long as it is a reagent that can introduce a group containing a fluorine atom into a carbonyl carbon atom. Among such fluorine reagents, trimethyl(trifluoromethyl)silane [TMS-$CF_3$], trifluoromethyl bromide [$CF_3Br$], and other trifluoromethylating agents and fluorinating agents are preferred.

A reaction can be performed under a conventional condition with reference to the type of the fluorine reagent. For example, when TMS-$CF_3$ is used, the reaction is preformed in an appropriate solvent, such as tetrahydrofuran, and preferably in the presence of a catalyst such as a quaternary ammonium salt. The quaternary ammonium salt includes, for example, tetrabutylammonium fluoride. A reaction temperature is from about −10° C. to about 50° C. The amount of the trifluoromethylating agent is, for example, from about 0.9 to about 1.5 moles per mole of the compound represented by Formula (d). After the completion of the reaction, the resulting reaction mixture is quenched by adding, for example, diluted hydrochloric acid, and the target compound can be separated and purified by a separation means such as extraction, distillation, crystallization, recrystallization, and column chromatography. The reagent $CF_3Br$ is generally used in combination with $Zn/PdCl_2(PPh_3)$, $Zn/Cp_2TiCl_2$, Zn/pyridine, or Zn/tetrabutylammonoium fluoride, for example.

When the trifluoromethylating agent is used as the fluorine reagent, compounds represented by Formula (b1) where $R^x$ is a trifluoromethyl group are obtained under normal conditions.

Compounds represented by Formula (b1) where $R^d$ is a hydroxyl-protecting group can be produced by subjecting compounds where $R^d$ is a hydrogen atom, which are obtained according to the above procedure, to a reaction for introducing a protecting group according to the type of the protecting group. Such reactions for introducing a protecting group include conventional reactions generally employed in the field of organic synthesis.

[Compounds Represented by Formula (c1) and Production Thereof]

The compounds represented by Formula (c1) correspond to compounds represented by Formula (c) in which the two $R^{w2}$s are groups containing a fluorine atom. In Formula (c1), the groups containing a fluorine atom in $R^x$ and $R^{y1}$ include, for example, fluorine atom and trifluoromethyl group.

Each of the monomers containing a fluorine atom and having an ethylenic double bond represented by Formula (c1) can be produced by allowing the cyclic thioester having an ethylenic double bond represented by Formula (e) to react with a fluorine reagent. The symbols in Formula (e) have the same meanings as above.

Such fluorine reagents are not specifically limited as long as they are reagents that can convert a thiocarbonyl group into a methylene group having a group containing a fluorine atom. Among them, diethylaminosulfur trifluoride (DAST) tetrabutylammonium fluoride-$(HF)_2$, $TBA^+H_2F_3^-$/N-bromosuccinimide, and other fluorinating agents (reagents for introducing a fluorine atom) and trifluoromethylating agents are preferred. The term "$TBA^+$" means a tetrabutylammonium ion.

A reaction can be performed under a conventional condition with reference to the type of the fluorine reagent. For example, when a fluorinating agent is used as the fluorine reagent, the reaction is performed in an appropriate solvent such as methylene chloride at a temperature of from about −70° C. to about 50° C. The amount of the fluorinating agent is from about 0.9 to about 5 moles per mole of the compound represented by Formula (e) After the completion of the reaction, the target compound can be separated and purified by a separation means such as extraction, distillation, crystallization, recrystallization, or column chromatography. When the fluorinating agent is used, compounds represented by Formula (c1) in which $R^x$ and $R^{y1}$ are fluorine atoms are obtained under normal conditions.

[Compounds Represented by Formula (e)]

Each of the monomers having a cyclic thioester skeleton represented by Formula (e) can be produced, for example, by allowing a corresponding compound having a cyclic ester (lactone) skeleton to react with a sulfurizing agent. Such sulfurizing agents are not specifically limited as long as they can convert a carbonyl group into a thiocarbonyl group. Among them, 2,4-bis(4-methoxyphenyl)-1,3,2,4-dithiadiphosphetane 2,4-disulfide (Lawesson reagent) is typically preferred. A reaction is performed in an appropriate solvent such as toluene at a temperature of from about 50° C. to about 200° C. The amount of the sulfurizing agent is from about 0.9 to about 2 moles per mole of the lactone. After the completion of the reaction, the polymerizable cyclic compound represented by Formula (e) can be separated and purified by a separation means such as extraction, distillation, crystallization, recrystallization, or column chromatography.

Typical examples of the compounds represented by Formula (e) include compounds represented by Formula (3a) mentioned later.

[Polymerizable Bridged Cyclic Compounds (1) Containing a Fluorine Atom]

In the polymerizable bridged cyclic compounds each containing a fluorine atom represented by Formula (1), $R^a$, $R^b$, and $R^c$ are the same or different and are each a hydrogen atom or an organic group. Such organic groups are similar to those mentioned above.

Preferred $R^a$, $R^b$, and $R^c$ include hydrogen atom; methyl, ethyl, propyl, isopropyl, butyl, and other $C_1$–$C_{10}$ aliphatic hydrocarbon groups (specifically, $C_1$–$C_4$ alkyl groups); alicyclic hydrocarbon groups (specifically, $C_3$–$C_{15}$ cycloalkyl groups or cycloalkenyl groups); $C_6$–$C_{14}$ aryl groups; trifluoromethyl group and other halogenated hydrocarbon groups; fluorine atom, chlorine atom, and other halogen atoms. Alternatively, $R^a$ and $R^b$ are preferably combined to form a non-aromatic carbocyclic ring containing from about 3 to about 15 members (typically from about 5 to about 10 members) with the adjacent carbon atom. Typically preferred $R^a$, $R^b$, and $R^c$ are hydrogen atoms or methyl groups.

The ethenyl group having $R^a$, $R^b$, and $R^c$ in Formula (1) may be combined with any of carbon atoms constituting a bridged ring but is often combined with a carbon atom at a bridgehead position. The bonding position of the ethenyl group or its precursor (e.g., a hydroxyalkyl group in Formula (4) or an acyl group in Formula (6)) in starting materials and intermediates mentioned later is similar to that in Formula (1).

In the polymerizable bridged cyclic compounds containing a fluorine atom represented by Formula (1), $R^x$ is a trifluoromethyl group and $R^y$ is a —$OR^d$ group, where $R^d$ is hydrogen atom or a hydroxyl-protecting group, when Z is a single bond. $R^x$ and $R^y$ are fluorine atoms when Z is an oxygen atom. Specifically, the compounds represented by Formula (1) include the trifluoromethyladamantane derivatives represented by Formula (1a) and 2,2-difluoro-3-oxatricyclo[4.3.1.1$^{4,8}$]undecane derivatives represented by Formula (1b).

The hydroxyl-protecting group in $R^d$ is similar to that mentioned above.

Carbon atoms constituting the ring in Formula (1) (carbon atoms at bridgehead positions and/or carbon atoms at non-bridgehead positions) may each have a substituent. Such substituents include, but are not limited to, methyl group, ethyl group, isopropyl group, and other $C_1$–$C_4$ alkyl groups, hydroxyl group which may be protected by a protecting group, hydroxyalkyl groups which may be protected by a protecting group, carboxyl group which may be protected by a protecting group, amino group which may be protected by a protecting group, halogen atoms, oxo group, nitro group, and halogenated alkyl groups such as trifluoromethyl group. As the protecting groups, conventional protecting groups in the field of organic synthesis can be used. When starting materials or intermediates used in production of the polymerizable bridged cyclic compounds containing a fluorine atom of the present invention are compounds each having a ring, carbon atoms constituting the ring may each have a substituent. Such substituents include the aforementioned substituents.

Typical examples of the polymerizable bridged cyclic compounds each containing a fluorine atom represented by Formula (1) include 2-trifluoromethyl-2-hydroxy-5-vinyladamantane, 2-trifluoromethyl-2-methoxy-5-vinyladamantane, 2-trifluoromethyl-2-hydroxy-5-(1-propenyl)adamantane, 2-trifluoromethyl-2-hydroxy-5-(1-methylethenyl)adamantane, and other adamantane derivatives each having a trifluoromethyl group and a hydroxyl group which may be protected by a protecting group at the 2-position and an ethylenic double bond at the 5-position; 2,2-difluoro-6-vinyl-3-oxatricyclo[4.3.1.1$^{4,8}$]undecane, 2,2-difluoro-6-(1-propenyl)-3-oxatricyclo[4.3.1.1$^{4,8}$]undecane, 2,2-difluoro-6-(1-methylethenyl)-3-oxatricyclo[4.3.1.1$^{4,8}$]undecane, and other 3-oxatricyclo[4.3.1.1$^{4,8}$]undecane derivatives each having two fluorine atoms at the 2-position and an ethylenic double bond at the 6-position; 2,2-bis(trifluoromethyl)-6-vinyl-3-oxatricyclo[4.3.1.1$^{4,8}$]undecane, 2,2-bis(trifluoromethyl)-6-(1-propenyl)-3-oxatricyclo[4.3.1.1$^{4,8}$]undecane, 2,2-bis(trifluoromethyl)-6-(1-methylethenyl)-3-oxatricyclo[4.3.1.1$^{4,8}$]undecane, and other 3-oxatricyclo[4.3.1.1$^{4,8}$]undecane derivatives each having two trifluoromethyl groups at the 2-position and an ethylenic double bond at the 6-position.

The compounds represented by Formula (1) each have a polymerizable ethylenic double bond, contain a bridged cyclic skeleton and a fluorine atom that impart various functions to the compounds and are therefore very useful as, for example, monomers for functional polymers.

[Production of Polymerizable Bridged Cyclic Compounds (1) Containing a Fluorine Atom]

The compounds represented by Formula (1) include the compounds represented by Formula (1a) and the compounds represented by Formula (1b).

Of the adamantane derivatives each containing a fluorine atom and having an ethylenic double bond represented by Formula (1a), a compound where $R^d$ is a hydrogen atom can be obtained, for example, by allowing the adamantanone derivative having an ethylenic double bond represented by Formula (2) to react with a fluorine reagent such as a trifluoromethylating agent.

$R^a$, $R^b$, and $R^c$ in Formula (2) have the same meanings as above. The fluorine reagent is not specifically limited as long as it is a reagent that can introduce a group containing a fluorine atom into a carbonyl carbon atom. Among such fluorine reagents, trimethyl(trifluoromethyl)silane [TMS-$CF_3$] and other trifluoromethylating agents are preferred.

A reaction can be performed in the same manner as in the production of the compounds represented by Formula (b1). When the trifluoromethylating agent is used as the fluorine reagent, compounds represented by Formula (1a) in which $R^x$ is a trifluoromethyl group can be obtained.

Adamantane derivatives each containing a fluorine atom and having an ethylenic double bond represented by Formula (1a) where $R^d$ is a hydroxyl-protecting group can be produced by subjecting compounds where $R^d$ is a hydrogen atom, which are obtained according to the above procedure, to a reaction for introducing a protecting group according to the type of the protecting group. Such reactions for introducing a protecting group include conventional reactions generally employed in the field of organic synthesis.

Each of the 3-oxatricyclo[4.3.1.1$^{4,8}$]undecane derivatives containing a fluorine atom and having an ethylenic double bond represented by Formula (1b) can be produced, for example, by allowing the 3-oxatricyclo[4.3.1.1$^{4,8}$]undecane-2-thione derivative having an ethylenic double bond represented by Formula (3a) to react with a fluorine reagent.

$R^a$, $R^b$, and $R^c$ in Formula (3a) are similar to those mentioned above. The fluorine reagent is not specifically limited as long as it is a reagent that can convert a thiocarbonyl group into a methylene group having a group containing a fluorine atom. Among such fluorine reagents, diethylaminosulfur trifluoride (DAST) and other fluorinating agents (reagents for introducing a fluorine atom) are preferred.

A reaction can be performed in the same manner as in the production of the compounds represented by Formula (c1). When the fluorinating agent is used as the fluorine reagent, compounds represented by Formula (1b) in which $R^x$ and $R^y$ are fluorine atoms (2,2-difluoro-3-oxatricyclo[4.3.1.1$^{4,8}$] undecane derivatives) are obtained under normal conditions.

[Production of Compounds Represented by Formula (3a)]

Each of the 3-oxatricyclo[4.3.1.1$^{4,8}$]undecane-2-thione derivatives having an ethylenic double bond represented by Formula (3a) can be obtained, for example, by allowing the 3-oxatricyclo[4.3.1.1$^{4,8}$]undecan-2-one derivative represented by Formula (3b) to react with a sulfurizing agent.

$R^a$, $R^b$, and $R^c$ in Formula (3b) are similar to those mentioned above. The sulfurizing agent is not specifically limited as long as it is a reagent that can convert a carbonyl group into a thiocarbonyl group. Among such sulfurizing agents, 2,4-bis(4-methoxyphenyl)-1,3,2,4-dithiadiphosphetane 2,4-disulfide (Lawesson reagent) is typically preferred.

A reaction is performed in an appropriate solvent such as toluene at a temperature of from about 50° C. to about 200° C. The amount of the sulfurizing agent is from about 0.9 to about 2 moles per mole of the 3-oxatricyclo[4.3.1.1$^{4,8}$]undecan-2-one derivative represented by Formula (3b). After the completion of the reaction, the target compound can be separated and purified by a separation means such as extraction, distillation, crystallization, recrystallization, or column chromatography.

Typical examples of the compounds represented by Formula (3a) thus obtained include 6-vinyl-3-oxatricyclo[4.3.1.1$^{4,8}$]undecane-2-thione, 6-(1-propenyl)-3-oxatricyclo[4.3.1.1$^{4,8}$]undecane-2-thione, 6-(1-methylethenyl)-3-oxatricyclo[4.3.1.1$^{4,8}$]undecane-2-thione, and other 3-oxatricyclo[4.3.1.1$^{4,8}$]undecane-2-thione derivatives each having an ethylenic double bond at the 6-position.

[Production of Compounds Represented by Formula (5)]

Each of the bridged cyclic compounds having an ethylenic double bond represented by Formula (5) (i.e., the compounds represented by Formula (2) and the compounds represented by Formula (3b)) can be obtained, for example, by subjecting the bridged cyclic compound containing a hydroxyalkyl group represented by Formula (4) to a dehydration reaction.

$R^a$, $R^b$, and $R^c$ in Formula (4) are similar to those mentioned above. Z is a single bond or an oxygen atom. When Z is a single bond, the bridged ring in the formula is an adamantane ring. When Z is an oxygen atom, the bridged ring in the formula is an 3-oxatricyclo[4.3.1.1$^{4,8}$]undecane ring.

The dehydration reaction is performed in an appropriate solvent such as toluene, where necessary in the presence of sulfuric acid or another acid or a dehydrating agent, at a temperature of from about 0° C. to about 150° C. The dehydration reaction may be performed while distilling off water which is by-produced as a result of azeotropy. After the completion of the reaction, the target compound can be separated and purified by a separation means such as extraction, distillation, crystallization, recrystallization, or column chromatography.

Typical examples of the compounds represented by Formula (5) thus obtained include 1-vinyladamantan-4-one, 1-(1-propenyl)adamantan-4-one, 1-(1-methylethenyl)adamantan-4-one, and other adamantan-4-one derivatives each having an ethylenic double bond at the 1-position; 6-vinyl-3-oxatricyclo[4.3.1.1$^{4,8}$]undecan-2-one, 6-(1-propenyl)-3-oxatricyclo[4.3.1.1$^{4,8}$]undecan-2-one, 6-(1-methylethenyl)-3-oxatricyclo[4.3.1.1$^{4,8}$]undecan-2-one, and other 3-oxatricyclo[4.3.1.1$^{4,8}$]undecan-2-one derivatives each having an ethylenic double bond at the 6-position.

[Production of Compounds Represented by Formula (4)]

Each of the bridged cyclic compounds each containing a hydroxyalkyl group represented by Formula (4) can be obtained, for example, by subjecting the bridged cyclic compound containing an acyl group represented by Formula (6) to reduction or to a reaction with the organometallic compound represented by Formula (9). When the bridged cyclic compound containing an acyl group represented by Formula (6) is reduced, compounds represented by Formula (4) in which $R^c$ is a hydrogen atom are obtained. When the bridged cyclic compound containing an acyl group represented by Formula (6) is subjected to a reaction with the organometallic compound represented by Formula (9), compounds represented by Formula (4) in which $R^c$ is $R^{c1}$ (an organic group) are obtained. $R^a$, $R^b$, and Z in Formula (6) are similar to those mentioned above.

The bridged cyclic compound containing an acyl group represented by Formula (6) can be reduced, for example, by reduction using a metal hydride complex compound such as lithium aluminium hydride or sodium borohydride; reduction using a borane; or catalytic reduction using hydrogen and a Rh catalyst. Reduction is performed in a solvent at a temperature of from about −100° C. to about 150° C. Such solvents are selected, depending on the type of the reduction process, from diethyl ether, tetrahydrofuran, and other ethers; hexane and other aliphatic hydrocarbons; cyclohexane and other alicyclic hydrocarbons; toluene and other aromatic hydrocarbons; methanol, ethanol, and other alcohols; acetic acid and other carboxylic acids; methylene chloride and other halogenated hydrocarbons. After the completion of the reaction, the resulting reaction mixture is quenched for example with water according to necessity, and the target compound can be separated and purified by a separation means such as extraction, distillation, crystallization, recrystallization, or column chromatography.

In the organometallic compounds represented by Formula (9), $R^{c1}$ is an organic group; and M is a metallic atom which may have a ligand, or the group represented by Formula (10). The organic group in $R^{c1}$ is similar to that in $R^c$.

The metallic atom in M includes, but is not limited to, lithium and other alkali metal atoms, cerium, titanium, copper, and other transition metal atoms. These metallic atoms may each have a ligand. The term "ligand" as used herein also means and includes atoms or atomic groups corresponding to cations in ate complexes. Such ligands include, for example, chlorine atom and other halogen atoms, isopropoxy group and other alkoxy groups, diethylamino group and other dialkyl amino groups, cyano group, alkyl groups, lithium atom and other alkali metal atoms (as cations in ate complexes). The halogen atom represented by $X^1$ in Formula (10) includes, for example, chlorine, bromine, and iodine atoms. Typical examples of the organometallic compounds represented by Formula (9) include dimethyldiisopropoxytitanium and other organic titanium compounds (including ate complexes of organic titanium), organic magnesium compounds (e.g., Grignard reagents), and organic lithium compounds.

The amount of the organometallic compound represented by Formula (9) is, for example, from about 0.9 to about 1.5 moles per mole of the bridged cyclic compound containing an acyl group represented by Formula (6). A reaction is usually performed in an organic solvent. Such organic solvents include, but are not limited to, the aforementioned ethers and aliphatic hydrocarbons. A reaction temperature can appropriately be selected within the range of from about −100° C. to about 150° C. depending on the type of the reaction components and other factors. After the completion of the reaction, the resulting reaction mixture is usually quenched with an aqueous solution containing an acid (e.g., hydrochloric acid) or a salt (e.g., ammonium chloride), and the alkalinity or acidity of the resulting mixture is adjusted according to necessity. Thereafter, the target compound can be separated and purified by a separation means such as filtration, concentration, extraction, distillation, crystallization, recrystallization, or column chromatography.

Typical examples of the compounds represented by Formula (4) thus obtained include 1-(1-hydroxyethyl)

adamantan-4-one, 1-(1-hydroxypropyl)adamantan-4-one, 1-(1-hydroxy-1-methylethyl)adamantan-4-one, and other adamantan-4-one derivatives each having a 1-hydroxyalkyl group at the 1-position; 6-(1-hydroxyethyl)3-oxatricyclo[4.3.1.1$^{4,8}$]undecan-2-one, 6-(1-hydroxypropyl)3-oxatricyclo[4.3.1.1$^{4,8}$]undecan-2-one, 6-(1-hydroxy-1-methylethyl)3-oxatricyclo[4.3.1.1$^{4,8}$]undecan-2-one, and other 3-oxatricyclo[4.3.1.1$^{4,8}$]undecan-2-one derivatives each having a 1-hydroxyalkyl group at the 6-position.

[Production of Compounds Represented by Formula (6)]

Each of the bridged cyclic compounds each containing an acyl group represented by Formula (6) can be obtained, for example, by allowing the bridged cyclic compound represented by Formula (7) to react with an acylating agent comprising (A) the 1,2-dicarbonyl compound or its hydroxy reductant represented by Formula (8), (B) oxygen, and (C) at least one compound selected from (c1) metallic compounds and (c2) N-hydroxy or N-oxo cyclic imide compounds.

Z in Formula (7) and R$^a$ and R$^b$ in Formula (8) are similar to those mentioned above. R in Formula (8) is a hydrogen atom or an organic group. The organic group in R is similar to the organic groups in R$^a$, R$^b$, and R$^c$. Z$^1$ and Z$^2$ are the same or different and are each an oxygen atom or a hydroxyl group, and the bond between a carbon atom and Z$^1$ or Z$^2$ is a single bond or a double bond.

The bridged cyclic compound represented by Formula (7) can be obtained according to a conventional procedure or a similar procedure thereto.

In the components (A), typical examples of the 1,2-dicarbonyl compounds include biacetyl(2,3-butanedione), 2,3-pentanedione, 3,4-hexanedione, acetylbenzoyl, and other α-diketones. Typical examples of the hydroxy reductants of the 1,2-dicarbonyl compounds include acetoin and other α-keto-alcohols; 2,3-butanediol, 2,3-pentanediol, and other vicinal diols.

Oxygen (B) may be either molecular oxygen or active oxygen (oxygen radical). The molecular oxygen includes, but is not limited to, pure oxygen, and oxygen diluted with an inert gas such as nitrogen, helium, argon or carbon dioxide, as well as air. As oxygen (B), molecular oxygen is frequently used.

Metallic elements to constitute the metallic compounds (C1) are not specifically limited, and can be any metallic element of Groups 1 to 15 of the Periodic Table of Elements. The term "metallic element" as used herein also means and includes boron, B. Examples of the metallic elements include, of the Periodic Table of Elements, Group 1 elements (e.g., Li, Na, and K), Group 2 elements (e.g., Mg, Ca, Sr, and Ba), Groups 3 elements (e.g., Sc, lanthanoid elements, and actinoid elements), Group 4 elements (e.g., Ti, Zr, and Hf), Group 5 elements (e.g., V), Group 6 elements (e.g., Cr, Mo, and W), Group 7 elements (e.g., Mn), Group 8 elements (e.g., Fe and Ru), Group 9 elements (e.g., Co and Rh), Group 10 elements (e.g., Ni, Pd, and Pt), Group 11 elements (e.g., Cu), Group 12 elements (e.g., Zn), Groups 13 elements (e.g., B, Al, and In), Group 14 elements (e.g., Sn and Pb), and Group 15 elements (e.g., Sb and Bi). Preferred metallic elements include transition metal elements (elements of Groups 3 to 12 of the Periodic Table of Elements). Among them, elements of the Groups 5 to 11 of the Periodic Table of Elements are preferred, of which Group 5 elements and Group 9 elements are typically preferred. Especially, Co and V can advantageously be used. The valence of the metallic element is not specifically limited and may range from about 0 to about 6.

The metallic compounds (C1) include, but are not limited to, elementary substances, hydroxides, oxides (including complex oxides), halides (fluorides, chlorides, bromides, and iodides), salts of oxoacids (e.g., nitrates, sulfates, phosphates, borates, and carbonates), oxoacids, isopoly acids, heteropoly acids, and other inorganic compounds of the aforementioned metallic elements; salts of organic acids (e.g., acetates, propionates, prussiates, naphthenates, and stearates), complexes, and other organic compounds of the metallic elements. Ligands constituting the complexes include OH (hydroxo), alkoxy (e.g., methoxy, ethoxy, propoxy, and butoxy), acyl (e.g., acetyl and propionyl), alkoxycarbonyl (e.g., methoxycarbonyl and ethoxycarbonyl), acetylacetonato, cyclopentadienyl group, halogen atoms (e.g., chlorine and bromine), CO, CN, oxygen atom, H$_2$O (aquo), phosphine(triphenylphosphine and other triarylphosphines) and other phosphorus compounds, NH$_3$ (ammine), NO, NO$_2$ (nitro), NO$_3$ (nitrate), ethylenediamine, diethylenetriamine, pyridine, phenanthroline, and other nitrogen-containing compounds.

Examples of the metallic compounds (C1) include, taking cobalt compounds as an example, cobalt hydroxide, cobalt oxide, cobalt chloride, cobalt bromide, cobalt nitrate, cobalt sulfate, cobalt phosphate, and other inorganic compounds; cobalt acetate, cobalt naphthenate, cobalt stearate, and other salts of organic acids; acetylacetonatocobalt, and other complexes, and other divalent or trivalent cobalt compounds. Example of the vanadium compounds include vanadium hydroxide, vanadium oxide, vanadium chloride, vanadyl chloride, vanadium sulfate, vanadyl sulfate, sodium vanadate, and other inorganic compounds; acetylacetonatovanadium, vanadyl acetylacetonato, and other complexes, and other vanadium compounds having a valence of 2 to 5. Examples of the compounds of the other metallic elements include compounds corresponding to the above-mentioned cobalt or vanadium compounds. Each of the metallic compounds (C1) can be used alone or in combination.

The ratio of the metallic compound (C1) to the 1,2-dicarbonyl compound or its hydroxy reductant (A) is, for example, such that the former (C1)/the latter (A) (by mole) is from about 0 to about 0.5, and preferably from about 0.001 to about 0.2.

The N-hydroxy or N-oxocyclicimide compounds (c2) include imide compounds represented by following Formula (11):

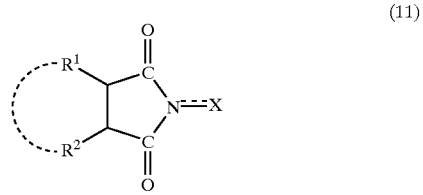

(11)

wherein R$^1$ and R$^2$ are the same or different and are each a hydrogen atom, a halogen atom, an alkyl group, an aryl group, a cycloalkyl group, a hydroxyl group, an alkoxy group, a carboxyl group, an alkoxycarbonyl group, or an acyl group, where R$^1$ and R$^2$ may be combined to form a double bond or an aromatic or non-aromatic ring; X is an oxygen atom or a hydroxyl group; and one or two of N-substituted cyclic imido group indicated in Formula (11) may further be formed on R$^1$, R$^2$, or on the double bond or aromatic or non-aromatic ring formed by R$^1$ and R$^2$.

Of the substituents R$^1$ and R$^2$ in the imide compounds represented by Formula (11), the halogen atom includes iodine, bromine, chlorine and fluorine. The alkyl group includes, but is not limited to, methyl, ethyl, propyl, hexyl, decyl, and other straight- or branched-chain alkyl groups each containing from about 1 to about 10 carbon atoms. The aryl group includes, for example, phenyl and naphthyl groups. The cycloalkyl group include, for example, cyclopentyl and cyclohexyl groups. The alkoxy group includes, for example, methoxy, ethoxy, isopropoxy, and other alkoxy groups each containing from about 1 to about 10 carbon atoms. The alkoxycarbonyl group includes, for example, methoxycarbonyl, ethoxycarbonyl, isopropoxycarbonyl, and other alkoxycarbonyl groups each containing from about 1 to about 10 carbon atoms in the alkoxy moiety. The acyl group includes, for example, formyl, acetyl, propionyl, butyryl, and other acyl groups each containing from about 1 to about 6 carbon atoms.

The substituents $R^1$ and $R^2$ may be identical to or different from each other. The substituents $R^1$ and $R^2$ in Formula (11) may be combined to form a double bond or an aromatic or non-aromatic ring. The preferred aromatic or non-aromatic ring has from about 5 to about 12 members, and specifically from about 6 to about 10 members. The ring may be a heterocyclic ring or condensed heterocyclic ring, but it is often a hydrocarbon ring. Such rings include, for example, non-aromatic alicyclic rings (e.g., cyclohexane ring and other cycloalkane rings which may have a substituent, cyclohexene ring and other cycloalkene rings which may have a substituent), non-aromatic bridged rings (e.g., 5-norbornene ring and other bridged hydrocarbon rings which may have a substituent), benzene ring, naphthalene ring, and other aromatic rings (including condensed rings) which may have a substituent. The ring is composed of an aromatic ring in many cases. The ring may have a substituent. Such substituents include, but are not limited to, alkyl groups, haloalkyl groups, hydroxyl group, alkoxy groups, carboxyl group, alkoxycarbonyl groups, acyl groups, nitro group, cyano group, amino group, and halogen atoms.

In Formula (11), X is an oxygen atom or a hydroxyl group, and the bond between the nitrogen atom N and X is a single bond or a double bond.

One or two of the N-substituted cyclic imido group indicated in Formula (11) may be further formed on $R^1$, $R^2$, or on the double bond or aromatic or non-aromatic ring formed by $R^1$ and $R^2$.

Preferred imide compounds include, for example, N-hydroxysuccinimide, N-hydroxymaleimide, N-hydroxyhexahydrophthalimide, N,N'-dihydroxycyclohexanetetracarboximide, N-hydroxyphthalimide, N-hydroxytetrabromophthalimide, N-hydroxytetrachlorophthalimide, N-hydroxychlorendimide, N-hydroxyhimimide, N-hydroxytrimellitimide, N,N'-dihydroxypyromellitimide, and N,N'-dihydroxynaphthalenetetracarboximide.

The imide compounds can be prepared by a conventional imidation process (a process for the formation of an imide), such as a process that comprises the steps of allowing a corresponding acid anhydride to react with hydroxylamine $NH_2OH$ for ring-opening of an acid anhydride group, and closing the ring to form an imide. Typically preferred imide compounds include N-hydroxyimide compounds derived from alicyclic polycarboxylic anhydrides or aromatic polycarboxylic anhydrides, of which N-hydroxyimide compounds derived from aromatic polycarboxylic anhydrides, for example, N-hydroxyphthalimide are specifically preferred. Each of these N-hydroxy or N-oxo cyclic imide compounds (c2) can be used alone or in combination.

The ratio of the N-hydroxy or N-oxo cyclic imide compound (c2) to the 1,2-dicarbonyl compound or its hydroxy reductant (A) is, for example, such that the former (C2)/the latter (A) is from about 0 to about 1, and preferably from about 0.00001 to about 0.5.

The acylating agent has only to contain at least one compound selected from the metallic compounds (C1) and the N-hydroxy or N-oxo cyclic imide compounds (C2). Specifically, the embodiments of the acylating agent include: (i) an acylating agent composed of the 1,2-dicarbonyl compound or its hydroxy reductant (A), oxygen (B) and the metallic compound (C1), (ii) an acylating agent composed of the 1,2-dicarbonyl compound or its hydroxy reductant (A), oxygen (B) and the N-hydroxy or N-oxo cyclic imide compound (C2), and (iii) an acylating agent composed of the 1,2-dicarbonyl compound or its hydroxy reductant (A), oxygen (B), the metallic compound (C1), and the N-hydroxy or N-oxo cyclic imide compound (C2).

In many cases, the use of an acylating agent containing the metallic compound (C1) yields a high conversion rate, and the use of an acylating agent containing the N-hydroxy or N-oxo cyclic imide compound (C2) yields an acyl group-containing compound with high selectivity. An acylating agent containing the N-hydroxy or N-oxo cyclic imide compound (C2) has a feature that when used in combination with a hydroxy reductant of the 1,2-dicarbonyl compound as the compound (A), the hydroxy reductant is immediately converted into a corresponding 1,2-dicarbonyl compound in a system, and an acylation reaction proceeds smoothly.

The acylating agent may further comprise additional components including radical generators, and radical reaction accelerators in addition to the components (A), (B) and (C). Such additional components include, for instance, halogens (e.g., chlorine and bromine), peracids (e.g., peracetic acid and m-chloroperbenzoic acid), and peroxides (e.g., hydrogen peroxide and hydroperoxide).

Upon production of the bridged cyclic compound containing an acyl group represented by Formula (6), the amount of the 1,2-dicarbonyl compound or its hydroxy reductant (A) is, for example, equal to or more than 1 mole (e.g., from about 1 to about 50 moles), preferably from about 1.5 to about 20 moles, and more preferably from about 3 to about 10 moles per mole of the compound represented by Formula (7). The 1,2-dicarbonyl compound or its hydroxy reductant (A) can also be used as a reaction solvent.

The amount of oxygen (B) is, usually, equal to or more than 0.5 mole (e.g., equal to or more than 1 mole), preferably from about 1 to about 100 moles, and more preferably from about 2 to about 50 moles, per mole of the compound represented by Formula (7). In many cases, excess moles of molecular oxygen to the compound represented by Formula (7) is used.

The amount of the metallic compound (C1) is, for example, from about 0.00001 to about 1 mole, and preferably from about 0.0001 to about 0.7 mole, per mole of the compound represented by Formula (7). The amount of the imide compound (C2) is, for example, from about 0.000001 to about 1 mole, preferably from about 0.00001 to about 0.7 mole, per mole of the compound represented by Formula (7).

A reaction is generally performed in an organic solvent. Such organic solvents include, but are not limited to, acetic acid, propionic acid, and other organic acids; acetonitrile, propionitrile, benzonitrile, and other nitrites; formamide, acetamide, dimethylformamide (DMF), dimethylacetamide, and other amides; t-butanol, t-amyl alcohol, and other alcohols; hexane, octane, and other aliphatic hydrocarbons; benzene, toluene, and other aromatic hydrocarbons; chloroform, dichloromethane, dichloroethane, carbon tetrachloride, chlorobenzene, trifluoromethylbenzene, and other halogenated hydrocarbons; nitrobenzene, nitromethane, nitroethane, and other nitro compounds; ethyl acetate, butyl acetate, and other esters; diethyl ether, diisopropyl ether, and other ethers; and mixtures of these solvents. As the solvent, acetic acid and other organic acids, benzonitrile and other nitrites, trifluoromethylbenzene and other halogenated hydrocarbons are frequently employed.

A reaction temperature can appropriately be selected with reference to the types of the reactants and other factors and is, for example, from about 0° C. to about 300° C., preferably from about 30° C. to about 250° C., more preferably from about 40° C. to about 200° C., and frequently from about 40° C. to about 150° C. The reaction can be carried out at ambient pressure or under a pressure (under a load).

The reaction can be performed in a batch system, semibatch system, continuous system or another conventional system, in the presence of, or under flow of, oxygen. After the completion of the reaction, reaction products can be separated and purified according to a procedure such as filtration, concentration, distillation, extraction, crystallization, recrystallization, column chromatography and other separation means, or any combination of these separation means.

The acylation process using the acylating agent introduces an acyl group corresponding to the 1,2-dicarbonyl compound into the bridged cyclic compound represented by Formula (7) predominantly at a bridgehead position.

Typical examples of the compounds represented by Formula (6) thus obtained include 1-acetyladamantan-4-one, 1-propionyladamantan-4-one, and other adamantan-4-one derivatives each having an acyl group at the 1-position; 6-acetyl-3-oxatricyclo[4.3.1.1$^{4,8}$]undecan-2-one, 6-propionyl-3-oxatricyclo[4.3.1.1$^{4,8}$]undecan-2-one, and other 3-oxatricyclo[4.3.1.1$^{4,8}$]undecan-2-one derivatives each having an acyl group at the 6-position.

[Compounds Represented by Formula (a1) and Production Thereof]

The compounds represented by Formula (a1) correspond to compounds represented by Formula (a) in which $R^w$ is a group containing a fluorine atom, and $R^v$ is a hydrogen atom or a hydroxyl-protecting group. $R^e$ in Formula (a1) corresponds to $R^s$ in Formula (a)

In Formula (a1), the group containing a fluorine atom in $R^z$ includes, but is not limited to, fluorine atom and trifluoromethyl group. The hydroxyl-protecting group in $R^f$ is similar to that in $R^d$.

Each of the monomers containing a fluorine atom and having an ethylenic double bond represented by Formula (a1) can be produced by allowing the cyclic compound containing an acyl group and having an ethylenic double bond represented by Formula (f) to react with a fluorine reagent, or by subjecting the cyclic compound containing an acyl group and having an ethylenic double bond represented by Formula (f) to a reaction with a fluorine reagent and to a subsequent reaction for introducing a protecting group.

The symbols in Formula (f) have the same meanings as above. The fluorine reagent is not specifically limited as long as it is a reagent that can introduce a group containing a fluorine atom into a carbonyl carbon atom. Among such fluorine reagents, trimethyl(trifluoromethyl)silane [TMS-CF$_3$] and other trifluoromethylating agents and fluorinating agents are preferred.

A reaction can be performed under a conventional condition with reference to the type of the fluorine reagent. For example, when the trifluoromethylating agent is used, the reaction is performed in an appropriate solvent such as tetrahydrofuran, preferably in the presence of a catalyst such as a quaternary ammonium salt. Such quaternary ammonium salts include, for example, tetrabutylammonium fluoride. A reaction temperature is from about −10° C. to about 50° C. The amount of the trifluoromethylating agent is, for example, from about 0.9 to about 1.5 mole per mole of the compound represented by Formula (f). After the completion of the reaction, the resulting reaction mixture is quenched, for example, with dilute hydrochloric acid, and the target compound can be separated and purified by a separation means such as extraction, distillation, crystallization, recrystallization, or column chromatography. When the trifluoromethylating agent is used, compounds represented by Formula (a1) in which $R^z$ is trifluoromethyl group are obtained under normal conditions.

Compounds represented by Formula (a1) where $R^f$ is a hydroxyl-protecting group can be produced by subjecting compounds where $R^f$ is a hydrogen atom, which are obtained according to the above procedure, to a reaction for introducing a protecting group according to the type of the protecting group. Such reactions for introducing a protecting group include conventional reactions employed in the field of organic synthesis.

[Compounds Represented by Formula (12) and Production Thereof]

The compounds represented by Formula (12) are typical examples of the monomers (polymerizable cyclic compounds) containing a fluorine atom and having an ethylenic double bond represented by Formula (a1). The symbols in Formula (12) have the same meanings as those in Formula (a1).

Each of the adamantane derivatives containing a fluorine atom and having an ethylenic double bond represented by Formula (12) can be produced by allowing the acyladamantane derivative having an ethylenic double bond represented by Formula (13) to react with a fluorine reagent, or by subjecting the acyladamantane derivative having an ethylenic double bond represented by Formula (13) to a reaction with a fluorine reagent and to a subsequent reaction for introducing a protecting group.

The fluorine reagent is not specifically limited as long as it is a reagent that can introduce a group containing a fluorine atom into a carbonyl carbon atom. Among such fluorine reagents, trimethyl(trifluoromethyl)silane [TMS-CF$_3$] and other trifluoromethylating agents are preferred.

A reaction can be performed in the same manner as in the production of the compound represented by Formula (1a) from the compound represented by Formula (2). Likewise, the reaction for introducing a protecting group into a hydroxyl group can be performed in the same manner as above.

The acyladamantane derivative having an ethylenic double bond represented by Formula (13) can be produced, for example, by allowing the adamantane derivative having an ethylenic double bond represented by Formula (14) to react with an acylating agent comprising (A1) a 1,2-dicarbonyl compound or its hydroxy reductant represented by Formula (15), (B) oxygen, and (C) at least one compound selected from (c1) metallic compounds and (c2) N-hydroxy or N-oxo cyclic imide compounds.

Typical examples of the adamantane derivatives having an ethylenic double bond represented by Formula (14) include 1-vinyladamantane, 1-(1-propenyl)adamantane, and 1-(1-methylethenyl)adamantane.

The organic groups in $R^e$ and R in Formula (15) include similar organic groups to those mentioned above. Among them, $R^e$ is preferably a hydrogen atom, methyl group, ethyl group, or trifluoromethyl group. $Z^1$ and $Z^2$ are the same or different and are each an oxygen atom or a hydroxyl group.

In the components (A1), typical examples of the 1,2-dicarbonyl compounds include biacetyl(2,3-butanedione), perfluorobiacetyl, 2,3-pentanedione, 3,4-hexanedione, acetylbenzoyl, and other α-diketones. Typical examples of the hydroxy reductants of the 1,2-dicarbonyl compounds include acetoin and other α-keto-alcohols; 2,3-butanediol, 2,3-pentanediol, and other vicinal diols.

The components oxygen (B), the metallic compounds (c1), and N-hydroxy or N-oxo cyclic imide compounds (c2) are the same as in the acylating agents for use in the production of the compounds represented by Formula (6). The acylation reaction can be performed in the same manner as in the production of the compounds represented by Formula (6).

Among the compounds represented by Formula (13), compounds (aldehydes) in which $R^e$ is a hydrogen atom can also be produced by reducing corresponding carboxylic acids according to a conventional procedure.

Typical examples of the adamantane derivatives containing a fluorine atom and having an ethylenic double bond represented by Formula (12) include
1-(1-trifluoromethyl-1-hydroxyethyl)-3-vinyladamantane,
1-(1-trifluoromethyl-1-hydroxymethyl)-3-vinyladamantane, and
1-[1,1-bis(trifluoromethyl)-1-hydroxymethyl]-3-vinyladaman tane.

[Compounds Represented by Formula (16)]

The compounds represented by Formula (16) are examples of compounds represented by Formulae (b), (b1), (c), and (c1) in which $R^a$ or $R^b$ is combined with a carbon atom constituting ring $A^2$ or with a carbon atom constituting ring $A^3$ to form a condensed ring.

Z, $R^x$, and $R^y$ in Formula (16) have the same meanings as above. Each of the compounds represented by Formula (16) can be produced by using a norbornene derivative or an 2-oxabicyclo[3.2.1$^{1,5}$]-6-octene derivative as a starting material according to a procedure similar to the production of the compounds represented by Formula (1).

Typical examples of the compounds represented by Formula (16) include
5-trifluoromethyl-5-hydroxybicyclo[2.2.1]-2-heptene, and
3,3-difluoro-2-oxabicyclo[3.2.1$^{1,5}$]-6-octene.

[Compounds Represented by Formula (17)]

The compounds represented by Formula (17) are typical examples of compounds represented by Formulae (a) and (a1) in which $R^a$ or $R^b$ is combined with a carbon atom constituting ring $A^1$ to form a condensed ring.

$R^e$, $R^f$, and $R^z$ in Formula (17) have the same meanings as defined above. Each of the compounds represented by Formula (17) can be produced by using a norbornene derivative as a starting material in the same manner as in the production of the compounds represented by Formula (12).

Typical examples of the compounds represented by Formula (17) include
5-(1-trifluoromethyl-1-hydroxymethyl)bicyclo[2.2.1]-2-heptene,
5-(1-trifluoromethyl-1-hydroxyethyl)bicyclo[2.2.1]-2-heptene,
5-(1-trifluoromethyl-1-trimethylsilyloxyethyl)bicyclo[2.2.1]-2-heptene,
5-[1-trifluoromethyl-1-(1-ethoxyethyloxy)ethyl]bicyclo[2.2.1]-2-heptene,
5-[1,1-bis(trifluoromethyl)-1-hydroxymethyl]bicyclo[2.2.1]-2-heptene, and
5-(1-trifluoromethyl-1-hydroxy-1-(norborn-2-yl)methyl) bicyclo[2.2.1]-2-heptene.

[Compounds Represented by Formula (g1) and Production Thereof]

The compounds represented by Formula (g1) correspond to compounds represented by Formula (g) in which $R^w$ is a group containing a fluorine atom and $R^v$ is a hydrogen atom or a hydroxyl-protecting group. $R^e$ in Formula (g1) corresponds to $R^s$ in Formula (g).

In Formula (g1), the group containing a fluorine atom in $R^z$ includes, for example, fluorine atom and trifluoromethyl group. The hydroxyl-protecting group in $R^f$ is similar to that in $R^d$.

Each of the compounds containing a fluorine atom and having an ethylenic double bond represented by Formula (g1) can be produced by allowing the cyclic compound containing an acyl group and having an ethylenic double bond represented by Formula (k) to react with a fluorine reagent, or by subjecting the cyclic compound containing an acyl group and having an ethylenic double bond represented by Formula (k) to a reaction with a fluorine reagent and to a subsequent reaction for introducing a protecting group.

The symbols in Formula (k) have the same meanings as above. The fluorine reagent is not specifically limited as long as it is a reagent that can introduce a group containing a fluorine atom into a carbonyl carbon atom. Among such fluorine reagents, trimethyl(trifluoromethyl)silane [TMS-CF$_3$] and other trifluoromethylating agents and fluorinating agents are preferred.

A reaction can be performed under a conventional condition with reference to the type of the fluorine reagent. For example, when a trifluoromethylating agent is used, the reaction is performed in an appropriate solvent such as tetrahydrofuran, preferably in the presence of a catalyst such as a quaternary ammonium salt. Such quaternary ammonium salts include, for example, tetrabutylammonium fluoride. A reaction temperature is from about −10° C. to about 50° C. The amount of the trifluoromethylating agent is, for example, from about 0.9 to about 1.5 mole per mole of the compound represented by Formula (k). After the completion of the reaction, the resulting reaction mixture is quenched, for example, with dilute hydrochloric acid, and the target compound can be separated and purified by a separation means such as extraction, distillation, crystallization, recrystallization, or column chromatography. When the trifluoromethylating agent is used, compounds represented by Formula (g1) in which $R^z$ is a trifluoromethyl group are obtained under normal conditions.

Compounds represented by Formula (g1) where $R^f$ is a hydroxyl-protecting group can be produced by subjecting compounds where $R^f$ is a hydrogen atom, which are obtained according to the above procedure, to a reaction for introducing a protecting group according to the type of the protecting group. Such reactions for introducing a protecting group include conventional reactions employed in the field of organic synthesis.

[Compounds Represented by Formula (g2) and Production Thereof]

The compounds represented by Formula (g2) correspond to compounds represented by Formula (g) in which $R^s$ and $R^w$ are groups containing a fluorine atom, $R^v$ is a hydrogen atom or a hydroxyl-protecting group, and $W^2$ is an oxygen atom or a sulfur atom.

In Formula (g2), the group containing a fluorine atom in $R^{w5}$ includes, for example, fluorine atom and trifluoromethyl group. The hydroxyl-protecting group in $R^f$ is similar to that in $R^d$.

Each of the monomers containing a fluorine atom and having an ethylenic double bond represented by Formula (g2) can be produced by allowing the cyclic compound containing a hydroxyl group or mercapto group and having an ethylenic double bond represented by Formula (1) to react with the carbonyl compound containing a fluorine atom represented by Formula (m), or by subjecting the cyclic compound containing a hydroxyl group or mercapto group and having an ethylenic double bond represented by Formula (1) to a reaction with the carbonyl compound containing a fluorine atom represented by Formula (m) and to a subsequent reaction for introducing a protecting group.

In Formula (1), $W^{2a}$ is an oxygen atom or a sulfur atom, and the other symbols have the same meanings as above. The group containing a fluorine atom in $R^{w5}$ in Formula (m) is similar to that in $R^x$. A typical example of the carbonyl compounds containing a fluorine atom represented by Formula (m) is hexafluoroacetone.

The reaction between the cyclic compound containing a hydroxyl group or mercapto group and having an ethylenic double bond represented by Formula (1) and the carbonyl compound containing a fluorine atom represented by Formula (m) is performed under an appropriate condition with reference to the types of the reaction materials and other factors. For example, a reaction temperature is from about −10° C. to about 50° C. The amount of the carbonyl compound containing a fluorine atom represented by Formula (m) is from about 0.9 to about 1.5 moles per mole of the compound represented by Formula (1). The reaction yields a corresponding monomer containing an electron-withdrawing group represented by Formula (g2).

Compounds represented by Formula (g2) where $R^f$ is a hydroxyl-protecting group can be produced by subjecting compounds where $R^f$ is a hydrogen atom, which are obtained according to the above procedure, to a reaction for introducing a protecting group according to the type of the protecting group. Such reactions for introducing a protecting group include conventional reactions employed in the field of organic synthesis.

[Compounds Represented by Formula (18) and Others]

The compounds represented by Formula (18) are typical examples of compounds represented by Formula (g1) in which $R^a$ or $R^b$ is combined with a carbon atom constituting ring $A^4$ to form a condensed ring. The symbols in Formula (18) have the same meanings as above. The compounds represented by Formula (18) can be produced according to a similar process to that in the production of the compounds represented by Formula (g1) or in the production of the compounds represented by Formula (g2).

Typical examples of the compounds represented by Formula (18) include

5-[1,1-bis(trifluoromethyl)-1-hydroxymethyl]oxybicyclo[2.2.1]-2-heptene,

5-[1,1-bis(trifluoromethyl)-1-hydroxymethyl]oxymethylbicyclo[2.2.1]-2-heptene, and 5-hydroxy-6-[1,1-bis(trifluoromethyl)-1-hydroxymethyl]oxybicyclo[2.2.1]-2-heptene.

In the present invention, compounds corresponding to the compounds represented by Formula (18) in which the bicyclo[2.2.1]-2-heptene ring (bicyclo[2.2.1]-2-hepten-5-yl group) is replaced by a 1-vinyladamantane ring (1-vinyladamant-3-yl group) are also preferred. These compounds correspond to compounds represented by Formula (g1) in which $W^1$ is a single bond and ring $A^4$ is an adamantane ring. They can be produced in a similar process to that in the production of the compounds represented by Formula (g1) or in the production of the compounds represented by Formula (g2). Typical examples of the compounds in question include 1-[1,1,-bis(trifluoromethyl)-1-hydroxymethyl]oxy-3-vinyladamantane and 1-[1,1-bis(trifluoromethyl)-1-hydroxymethyl]oxymethyl-3-vinyladamantane.

[Compounds Represented by Formula (h1) and Production Thereof]

The compounds represented by Formula (h1) correspond to compounds represented by Formula (h) in which the two $R^{w2}$ s are groups containing a fluorine atom. The groups containing a fluorine atom in $R^x$ and $R^{y1}$ in Formula (h1) include, for example, fluorine atom and trifluoromethyl group.

Each of the monomers containing a fluorine atom and having an ethylenic double bond represented by Formula (h1) can be produced by allowing the cyclic compound containing a thiocarbonyl group and having an ethylenic double bond represented by Formula (n) to react with a fluorine reagent. The symbols in Formula (n) have the same meanings as above. As the fluorine reagent, those mentioned above can be used. A reaction can be performed in a conventional condition with reference to the type of the fluorine reagent. When a fluorinating agent is used as the fluorine reagent, the reaction is performed in an appropriate solvent such as methylene chloride at a temperature of from about −70° C. to about 50° C. The amount of the fluorinating agent is from about 0.9 to about 5 moles per mole of the compound represented by Formula (n). After the completion of the reaction, the target compound can be separated and purified by a separation means such as extraction, distillation, crystallization, recrystallization, or column chromatography. When the fluorinating agent is used, compounds represented by Formula (h1) in which $R^x$ and $R^{y1}$ are fluorine atoms are obtained under normal conditions.

[Compounds Represented by Formula (19)]

The compounds represented by Formula (19) are typical examples of compounds represented by Formula (h1) in which $R^a$ or $R^b$ is combined with a carbon atom constituting ring $A^5$ to form a condensed ring. The symbols in Formula (19) have the same meanings as above. The compounds represented by Formula (19) can be produced in the same manner as in the production of the compounds represented by Formula (h1).

Typical examples of the compounds represented by Formula (19) include 8,8-difluoro-7,9-dithiatricyclo[4.3.0.1$^{2,5}$]-3-decene, 8,8-difluoro-7,9-dioxatricyclo[4.3.0.1$^{2,5}$]-3-decene, and 8,8-bis(trifluoromethyl)-7,9-dioxatricyclo[4.3.0.1$^{2,5}$]-3-decene.

[Compounds Represented by Formula (20)]

The compounds represented by Formula (20) are typical examples of compounds represented by Formula (h1) in which $R^a$ or $R^b$ is combined with a carbon atom constituting ring $A^5$ to form a condensed ring and $G^2$ is a single bond, or compounds represented by Formula (c1) in which $R^a$ or $R^b$ is combined with a carbon atom constituting ring $A^3$ to form a condensed ring. The symbols in Formula (20) have the same meanings as above. The compounds represented by Formula (20) can be produced in the same manner as in the production of the compounds represented by Formula (h1) or in the production of the compounds represented by Formula (c1).

Typical examples of the compounds represented by Formula (20) include 7,7-difluoro-8-thiatricyclo[4.3.0.1$^{2,5}$]-3-decene, 7,7,9,9-tetrafluoro-8-thiatricyclo[4.3.0.1$^{2,5}$]-3-decene, 7,7-difluoro-8-oxatricyclo[4.3.0.1$^{2,5}$]-3-decene, and 7,7,9,9-tetrafluoro-8-oxatricyclo[4.3.0.1$^{2,5}$]-3-decene.

[Compounds Represented by Formula (i1) and Production Thereof]

The compounds represented by Formula (i1) correspond to compounds represented by Formula (i) in which the two $R^{w3}$s are groups containing a fluorine atom. In Formula (i1), the groups containing a fluorine atom in $R^x$ and $R^{y1}$ include, for example, fluorine atom and trifluoromethyl group.

Each of the monomers containing a fluorine atom and having an ethylenic double bond represented by Formula (i1) can be produced by allowing the cyclic compound containing a thiocarbonyl group and having an ethylenic double bond represented by Formula (o) to react with a fluorine reagent. The symbols in Formula (o) have the same meanings as above. As the fluorine reagent, those mentioned above can be used. A reaction can be performed in a conventional condition with reference to the type of the fluorine reagent. When a fluorinating agent is used as the fluorine reagent, the reaction is performed in an appropriate solvent such as methylene chloride at a temperature of from about −70° C. to about 50° C. The amount of the fluorinating agent is from about 0.9 to about 5 moles per mole of the compound represented by Formula (o). After the completion of the reaction, the target compound can be separated and purified by a separation means such as extraction, distillation, crystallization, recrystallization, or column chromatography. When the fluorinating agent is used, compounds represented by Formula (i1) in which $R^x$ and $R^{y1}$ are fluorine atoms are obtained under normal conditions.

[Compounds Represented by Formula (j1) and Production Thereof]

The compounds represented by Formula (j1) correspond to compounds represented by Formula (j) in which all the four $R^{w4}$s are groups containing a fluorine atom. In Formula (j1), the groups containing a fluorine atom in $R^x$ and $R^{y1}$ include, for example, fluorine atom and trifluoromethyl group.

Each of the monomers containing a fluorine atom and having an ethylenic double bond represented by Formula (j1) can be produced by allowing the cyclic compound containing a thiocarbonyl group and having an ethylenic double bond represented by Formula (p) to react with a fluorine reagent. The symbols in Formula (p) have the same meanings as defined above. As the fluorine reagent, those mentioned above can be used. A reaction can be performed in a conventional condition with reference to the type of the fluorine reagent. For example, when a fluorinating agent is used as the fluorine reagent, the reaction is performed in an appropriate solvent such as methylene chloride at a temperature of from about −70° C. to about 50° C. The amount of the fluorinating agent is from about 0.9 to about 5 moles per mole of the compound represented by Formula (p). After the completion of the reaction, the target compound can be separated and purified by a separation means such as extraction, distillation, crystallization, recrystallization, or column chromatography. When the fluorinating agent is used, compounds represented by Formula (j1) in which $R^x$ and $R^{y1}$ are fluorine atoms are obtained under normal conditions.

[Compounds Represented by Formula (21)]

The compounds represented by Formula (21) are typical examples of compounds represented by Formula (i1) in which m1=m2=0. The symbols in Formula (21) have the same meanings as defined above. The compounds represented by Formula (21) can be produced in the same manner as in the production of the compounds represented by Formula (i1).

Typical examples of the compounds represented by Formula (21) include 2,2-difluoro-1,3-dioxolene and 2,2-difluoro-1,3-dithiolene.

[Compounds Represented by Formula (22)]

The compounds represented by Formula (22) are typical examples of compounds represented by Formula (j1) in which m1=m2=0. The symbols in Formula (22) have the same meanings as above. The compounds represented by Formula (22) can be produced in the same manner as in the production of the compounds represented by Formula (j1).

Typical examples of the compounds represented by Formula (22) include 2,2,5,5-tetrafluoro-1-oxolene and 2,2,5,5-tetrafluoro-1-thiolene.

[Compounds in Which $W^1$ is an Ester Bond]

Each of the compounds represented by Formulae (a), (b), (c), (g), and (h) in which $W^1$ is an ester bond can be produced by preparing a compound of Formula (a), (b), (c), (g), or (h) in which a hydroxyl group is bonded instead of $W^1$ in the same manner as in the production of the compound represented by Formula (a), (b), (c), (g), or (h), and allowing the resulting compound to react with a carboxylic acid having a polymerizable unsaturated group, such as (meth) acrylic acid, or its reactive derivative. Conventional esterification reactions can be applied to this reaction.

The monomers of the present invention each preferably have a molecular weight of less than or equal to 800 (e.g., from about 80 to about 800), and more preferably less than or equal to 500 (e.g., from about 80 to about 500).

[Polymeric Compounds for Use in Photoresists]

The polymeric compounds for use in photoresists of the present invention include polymers each containing at least one of constitutional repeating units represented by Formula (G), (H), (I) or (J). The symbols in these formulae have the same meanings as in corresponding Formula (g), (h), (i) or (j). The polymeric compounds for use in photoresists of the present invention each contain an electron-withdrawing group such as a fluorine atom, have a specific cyclic structure and can thereby yield very high sensitivity in patterning.

Each of the polymeric compounds for use in photoresists of the present invention can be produced by subjecting one or more monomers represented by Formula (g), (h), (i) or (j) corresponding to each constitutional repeating unit and where necessary additional copolymerizable compounds to a polymerization reaction. Such additional copolymerizable compounds can appropriately be selected from acrylic monomers, olefinic monomers (including cyclic olefinic monomers), and other polymerizable compounds with reference to desired functions. Such acrylic monomers include, but are not limited to, 2-trifluoromethylacrylic acid or its esters (e.g., t-butyl 2-trifluoromethylacrylate), and fluorinated alkyl esters of (meth)acrylic acid. The olefinic monomers include, but are not limited to, norbornene and norbornene derivatives each having a group containing a fluorine atom (including a fluorine atom itself) combined to its ring. Polymerization can be performed according to a conventional procedure for use in the production of olefinic polymers or acrylic polymers, such as solution polymerization or melt polymerization.

In addition, preferred polymeric compounds for use in photoresists also include polymers obtained by (co-)polymerizing at least one selected from the monomers containing an electron-withdrawing group represented by Formula (a), the monomers containing an electron-withdrawing group represented by Formula (b), the monomers containing an electron-withdrawing group represented by Formula (c), the monomers having a cyclic thioester skeleton represented by Formula (e), the adamantanone derivatives having an ethylenic double bond represented by Formula (2), the 3-oxatricyclo[4.3.1.1$^{4,8}$]undecane derivatives having an ethylenic double bond represented by Formula (3), and the acyladamantane derivatives having an ethylenic double bond represented by Formula (13) or by copolymerizing at least one of these monomers and an additional polymerizable compound. Such additional polymerizable compounds include similar compounds mentioned above. Polymerization can be performed according to a conventional procedure for use in the production of olefinic polymers or acrylic polymers, such as solution polymerization or melt polymerization.

[Photosensitive Resin Compositions, Patterning Process and Process for Manufacturing Semiconductors]

The photosensitive resin compositions of the present invention each contain at least the polymeric compound for use in photoresists and a photosensitive acid generator.

Such photosensitive acid generators include conventional or known compounds that efficiently generate an acid upon irradiation with light. Such compounds include, but are not limited to, diazonium salts, iodonium salts (e.g., diphenyliodoniumhexafluorophosphate), sulfonium salts (e.g., triphenylsulfonium hexafluoroantimonate, triphenylsulfonium hexafluorophosphate, and triphenylsulfonium methanesulfonate), sulfonic acid esters [e.g., 1-phenyl-1-(4-methylphenyl)sulfonyloxy-1-benzoylmethane, 1,2,3-trisulfonyloxymethylbenzene, 1,3-dinitro-2-(4-phenylsulfonyloxymethyl)benzene, and 1-phenyl-1-(4-methylphenylsulfonyloxymethyl)-1-hydroxy-1-benzoylmethane], oxathiazol derivatives, s-triazine derivatives, disulfone derivatives (e.g., diphenyldisulfone), imide compounds, oxime sulfonates, diazonaphthoquinone, and benzointosylate. Each of these photosensitive acid generators can be used alone or in combination.

The amount of the photosensitive acid generator can appropriately be selected depending on the strength of the acid generated by light irradiation, the proportions of the individual constitutional repeating units in the polymeric compound and is, for example, from about 0.1 to about 30 parts by weight, preferably from about 1 to about 25 parts by weight, and more preferably from about 2 to 20 parts by weight, relative to 100 parts by weight of the polymeric compound for use in photoresists.

The photosensitive resin composition may further comprise additional components. Such additional components include, but are not limited to, alkali-soluble resins (e.g., novolak resins, phenol resins, imide resins, and carboxyl-group-containing resins), and other alkali-soluble components, coloring agents (e.g., dyestuffs), and organic solvents (e.g., hydrocarbons, halogenated hydrocarbons, alcohols, esters, amides, ketones, ethers, Cellosolves, Carbitols, glycol ether esters, and mixtures of these solvents) The patterning process of the present invention comprises at least the steps of applying the photosensitive resin composition to a substrate, applying light with a wavelength of less than or equal to 220 nm, baking, and developing. For example, the photosensitive resin composition is applied to a base or a substrate, is dried, and the resulting film (resist film) is exposed to light through a predetermined mask (or is further subjected to post-exposure baking) to form a latent image pattern, and the film is then developed, for example, by alkali aqueous solution and is selectively dissolved and removed the exposed part or the unexposed part to highly precisely yield a fine pattern.

Such substrates include, for example, silicon wafers, metals, plastics, glasses, and ceramics. The photoresist resin composition can be applied using a conventional application means such as a spin coater, a dip coater, and a roller coater. The applied film has a thickness of, for example, about 0.1 to about 20 µm, and preferably about 0.3 to about 2 µm.

Light rays with different wavelengths such as ultraviolet rays and X-rays can be applied. For example, g-line, i-line, and excimer laser (e.g., XeCl, KrF, KrCl, ArF, ArCl, or $F_2$ excimer laser) are usually used for semiconductor resists. Preferred wavelengths of these light sources are less than or equal to 220 nm (e.g., from 130 to 220 nm). The photosensitive resin composition of the present invention is specifically suitable for irradiation with $F_2$ laser light. An exposure energy is, for example, about 1 to about 1000 mJ/cm$^2$, and preferably about 10 to about 500 mJ/cm$^2$.

The process for producing a semiconductor of the present invention comprises at least the step of patterning according to the above patterning process. For example, a resist is patterned by the patterning process, and the substrate is etched by using the patterned resist as an etching mask to thereby yield a semiconductor (an electronic part).

INDUSTRIAL APPLICABILITY

The present invention provides novel monomers each having a cyclic skeleton and carrying an electron-withdrawing group and a polymerizable group, as well as processes for efficiently producing the same. These compounds can be used as monomers for functional polymers such as photoresist transparent polymeric compounds for use in photosensitive resin compositions.

The present invention also provides intermediates that are useful for the production of the monomers each having a cyclic skeleton and carrying an electron-withdrawing group and a polymerizable group, as well as processes for efficiently producing the same.

In addition, the polymeric compounds for use in photoresists, photosensitive resin composition, patterning process and process for producing a semiconductor according to the present invention can form very fine patterns with high precision, for example, using $F_2$ laser.

EXAMPLES

The present invention will be illustrated in further detail with reference to several examples below, which are not intended to limit the scope of the invention.

Example 1

Production of 6-acetyl-3-oxatricyclo[4.3.1.1$^{4,8}$]undecan-2-one

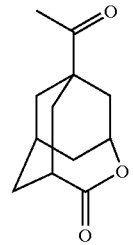

In a flask were placed 3-oxatricyclo[4.3.1.1$^{4,8}$]undecan-2-one (16.6 g, 100 mmol), acetylacetonatocobalt [Co(acac)$_2$] (50 mmol), 2,3-butanedione (600 mmol), and acetic acid (100 g). A condenser and an oxygen balloon were attached to the flask, and the mixture in the flask was vigorously stirred at 80° C. for 4 hours. After the completion of the reaction, the reaction mixture was concentrated, followed by addition of toluene and washing with water. The resulting organic layer was concentrated, the concentrate was subjected to silica gel column chromatography and thereby yielded the title compound 6-acetyl-3-oxatricyclo[4.3.1.1^{4,8}]undecan-2-one in a yield of 37%.

[Spectral Data]

MS m/e: 209 ([M+]), 171, 121.

Example 2

Production of 6-(1-hydroxyethyl)-3-oxatricyclo[4.3.1.1^{4,8}]undecan-2-one

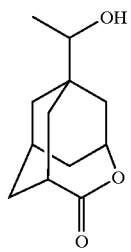

In a flask was placed 6-acetyl-3-oxatricyclo[4.3.1.1^{4,8}]undecan-2-one (20.8 g, 100 mmol) obtained by the procedure of Example 1, was treated with methanol (40 ml) and 0.1 N aqueous sodium hydroxide solution (6 ml), followed by gradual addition of sodium borohydride (NaBH$_4$) (50 mmol) and stirring for 30 minutes. After the completion of the reaction, the reaction mixture was neutralized with 1 N hydrochloric acid, was extracted with ethyl acetate, the organic layer was concentrated and thereby yielded the title compound 6-(1-hydroxyethyl)-3-oxatricyclo[4.3.1.1^{4,8}]undecan-2-one in a yield of 97%.

[Spectral Data]

MS m/e: 210 ([M+]), 165.

Example 3

Production of 6-vinyl-3-oxatricyclo[4.3.1.1^{4,8}]undecan-2-one

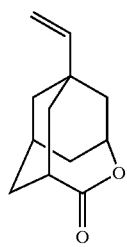

In a flask were placed 6-(1-hydroxyethyl)-3-oxatricyclo[4.3.1.1^{4,8}]undecan-2-one (21.0 g, 100 mmol) obtained by the procedure of Example 2, sulfuric acid (10 mmol), hydroquinone (21 mg), and toluene (200 g), and the resulting mixture was stirred for 4 hours under dehydration and reflux. After the completion of the reaction, the reaction mixture was washed with water, the organic layer was concentrated, the concentrate was subjected to silica gel column chromatography and thereby yielded the title compound 6-vinyl-3-oxatricyclo[4.3.1.1^{4,8}]undecan-2-one in a yield of 62%.

[Spectral Data]

MS m/e: 193 ([M+]), 155, 121.

Example 4

Production of 6-vinyl-3-oxatricyclo[4.3.1.1^{4,8}]undecane-2-thione

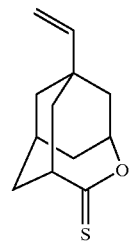

To a mixture of 6-vinyl-3-oxatricyclo[4.3.1.1^{4,8}]undecan-2-one (10 mmol) obtained by the procedure of Example 3 and toluene (50 ml) was added 2,4-bis(4-methoxyphenyl)-1,3,2,4-dithiadiphosphetane 2,4-disulfide [(p-MeO-C$_6$H$_4$P(=S)—S—)$_2$)] (10 mmol), and the resulting mixture was stirred at 110° C. for 24 hours. The reaction mixture was concentrated, the concentrate was subjected to silica gel column chromatography and thereby yielded the title compound 6-vinyl-3-oxatricyclo[4.3.1.1^{4,8}]undecane-2-thione in a yield of 75%.

[Spectral Data]

MS m/e: 209 ([M+]), 182, 177, 121.

Example 5

Production of 2,2-difluoro-6-vinyl-3-oxatricyclo[4.3.1.1$_{4,8}$]undecane

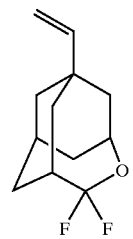

To a mixture of 6-vinyl-3-oxatricyclo[4.3.1.1^{4,8}]undecane-2-thione (2 mmol) obtained by the procedure of Example 4 and dry methylene chloride (10 ml) was added a solution of diethylaminosulfur trifluoride (DAST) in methylene chloride (1 M solution, 4 ml, 2 equivalents) using a syringe at room temperature in an atmosphere of nitrogen gas, followed by stirring for 24 hours. After the completion of the reaction, the resulting mixture was washed with an aqueous sodium hydrogen carbonate solution, and the organic layer was concentrated. The concentrate was subjected to silica gel column chromatography and thereby yielded the title compound 2,2-difluoro-6-vinyl-3-oxatricyclo[4.3.1.1$_{4,8}$]undecane in a yield of 52%.

[Spectral Data]

MS m/e: 231 ([M+]), 204, 188.

Example 6

Production of 1-acetyladamantan-4-one

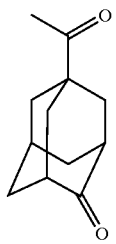

In a flask were placed 2-adamantanone (100 mmol), acetylacetonatocobalt [Co(acac)$_2$] (50 mmol), 2,3-butanedione (600 mmol), and acetic acid (100 g). A condenser and an oxygen balloon were attached to the flask, and the mixture in the flask was vigorously stirred at 80° C. for 4 hours. After the completion of the reaction, the reaction mixture was concentrated, was diluted with toluene and washing with water. The resulting organic layer was concentrated, the concentrate was subjected to silica gel column chromatography and thereby yielded the title compound 1-acetyladamantan-4-one in a yield of 21%.

[Spectral Data]

$^1$H-NMR (CDCl$_3$, TMS) δ: 2.4–1.5 (m, 13H), 2.1 (s, 3H).

MS m/e: 193 ([M$^+$]), 149, 121, 93, 79.

Example 7

Production of 1-(1-hydroxyethyl)adamantan-4-one

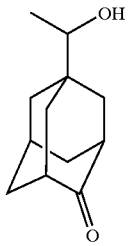

In a flask was placed 1-acetyladamantan-4-one (100 mmol) obtained by the procedure of Example 6 and was treated with methanol (40 ml) and 0.1 N aqueous sodium hydroxide solution (6 ml), followed by gradual addition of sodium borohydride (NaBH$_4$) (50 mmol) and stirring for 30 minutes. After the completion of the reaction, the reaction mixture was neutralized with 1 N hydrochloric acid, was extracted with ethyl acetate, the organic layer was concentrated and thereby yielded the title compound 1-(1-hydroxyethyl) adamantan-4-one in a yield of 52%.

[Spectral Data]

$^1$H-NMR (CDCl$_3$, TMS) δ: 3.3 (m, 1H), 2.4–1.4 (m, 14H), 1.1 (s, 3H).

MS m/e: 195 ([M$^+$]), 149.

Example 8

Production of 1-vinyladamantan-4-one

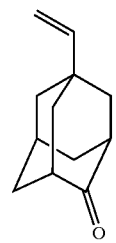

In a flask were placed 1-(1-hydroxyethyl)adamantan-4-one (100 mmol) obtained by the procedure of Example 7, sulfuric acid (10 mmol), hydroquinone (21 mg), and toluene (200 g), followed by stirring for 4 hours under dehydration and reflux. After the completion of the reaction, the reaction mixture was washed with water, the resulting organic layer was concentrated, the concentrate was subjected to silica gel column chromatography and thereby yielded the title compound 1-vinyladamantan-4-one in a yield of 78%.

[Spectral Data]

$^1$H-NMR (CDCl$_3$, TMS) δ: 5.7 (dd, 1H), 4.9–4.8 (m, 2H), 2.4–1.5 (m, 13H).

MS m/e: 177 ([M$^+$]), 161, 121.

Example 9

Production of 4-trifluoromethyl-4-hydroxy-1-vinyladamantane

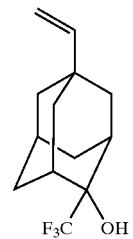

In tetrahydrofuran (THF) (30 ml) were dissolved 1-vinyladamantan-4-one (10 mmol) obtained by the procedure of Example 8 and trimethyl(trifluoromethyl)silane [TMS-CF$_3$] (12 mmol). The resulting solution was treated with 1M solution of tetrabutylammonium fluoride in THF (0.2 ml) at 0° C. with stirring. After its yellow color disappeared, the reaction mixture was stirred at room temperature for 24 hours. The mixture was then treated with 1N hydrochloric acid for 20 hours with stirring. The reaction mixture was concentrated, the concentrate was subjected to silica gel column chromatography and thereby yielded the title compound 4-trifluoromethyl-4-hydroxy-1-vinyladamantane in a yield of 54%.

[Spectral Data]

MS m/e: 247 ([M$^+$]), 178, 68.

$^{19}$F-NMR (CDCl$_3$) δ: −76.0.

Example 10

Production of 1-(1-trifluoromethyl-1-hydroxyethyl)-3-vinyladamantane

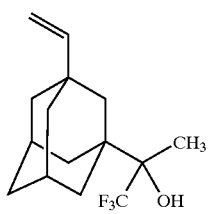

In a flask were placed 1-vinyladamantane (100 mmol), acetylacetonatocobalt [Co (acac)$_2$] (50 mmol), 2,3-butanedione (600 mmol), and acetic acid (100 g). A condenser and an oxygen balloon were attached to the flask, and the mixture in the flask was vigorously stirred at 80° C. for 4 hours. After the completion of the reaction, the reaction mixture was concentrated, was diluted with toluene and was washed with water. The resulting organic layer was concentrated, the concentrate was subjected to silica gel column chromatography and thereby yielded 1-acetyl-3-vinyladamantane in a yield of 36%.

[Spectral Data of 1-acetyl-3-vinyladamantane]

MS m/e: 205 ([M$^+$]), 152, 131.

In tetrahydrofuran (THF) (30 ml) were dissolved 1-acetyl-3-vinyladamantane (10 mmol) obtained by the above procedure and trimethyl(trifluoromethyl)silane [TMS-CF$_3$] (12 mmol). The resulting solution was treated with 1M solution of tetrabutylammonium fluoride in THF (0.2 ml) at 0° C. with stirring. After its yellow color disappeared, the reaction mixture was further stirred at room temperature for 24 hours. The mixture was then treated with 1N hydrochloric acid for 20 hours with stirring. The reaction mixture was concentrated, the concentrate was subjected to silica gel column chromatography and thereby yielded the title compound 1-(1-trifluoromethyl-1-hydroxyethyl)-3-vinyladamantane in a yield of 71%.

[Spectral Data]

MS m/e: 275 ([M$^+$]), 152, 68.

Example 11

Production of 5-(1-trifluoromethyl-1-hydroxymethyl)bicyclo[2.2.1]-2-heptene

According to the following reaction formula, 5-(1-trifluoromethyl-1-hydroxymethyl)bicyclo[2.2.1]-2-heptene was produced.

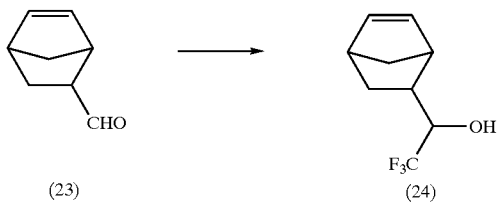

Initially, 5-formylbicyclo[2.2.1]-2-heptene (Formula (23), 10 mmol) and trimethyl(trifluoromethyl)silane [TMS-CF$_3$] (12 mmol) were dissolved in tetrahydrofuran (THF) (30 ml). The resulting solution was treated with 1M solution of tetrabutylammonium fluoride in THF (0.2 ml) at 0° C. with stirring. After its yellow color disappeared, the reaction mixture was further stirred at room temperature for 2 hours. The mixture was then treated with 1N hydrochloric acid for 20 hours with stirring. The reaction mixture was concentrated, the concentrate was subjected to silica gel column chromatography and thereby yielded 5-(1-trifluoromethyl-1-hydroxymethyl)bicyclo[2.2.1]-2-heptene represented by Formula (24) in a yield of 73%.

[Spectral Data]

MS m/e: 193 ([M$^+$]), 175, 68.

Example 12

Production of 5-trifluoromethyl-5-hydroxybicyclo[2.2.1]-2-heptene

According to the following reaction formula, 5-trifluoromethyl-5-hydroxybicyclo[2.2.1]-2-heptene was produced.

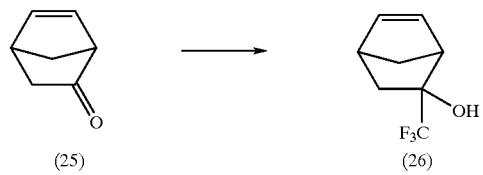

Initially, 5-oxobicyclo[2.2.1]-2-heptene (Formula (25), 10 mmol) and trimethyl(trifluoromethyl)silane [TMS-CF$_3$] (12 mmol) were dissolved in tetrahydrofuran (THF) (30 ml). The resulting solution was treated with 1M solution of tetrabutylammonium fluoride in THF (0.2 ml) at 0° C. with stirring. After its yellow color disappeared, the reaction mixture was further stirred at room temperature for 24 hours. The mixture was then treated with 1N hydrochloric acid for 20 hours with stirring. The reaction mixture was concentrated, the concentrate was subjected to silica gel column chromatography and thereby yielded 5-trifluoromethyl-5-hydroxybicyclo[2.2.1]-2-heptene represented by Formula (26) in a yield of 48%.

[Spectral Data]

MS m/e: 179 ([M$^+$]), 161, 68.

Example 13

[Production of 7,7-difluoro-4-methacryloyloxy-6-oxatricyclo[3.2.1.1$^{3,8}$]nonane According to the following reaction formula, 7,7-difluoro-4-methacryloyloxy-6-oxatricyclo[3.2.1.1$^{3,8}$]nonane represented by Formula (30) was produced.

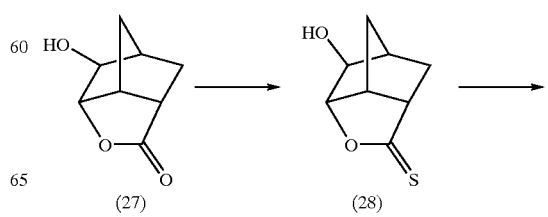

-continued

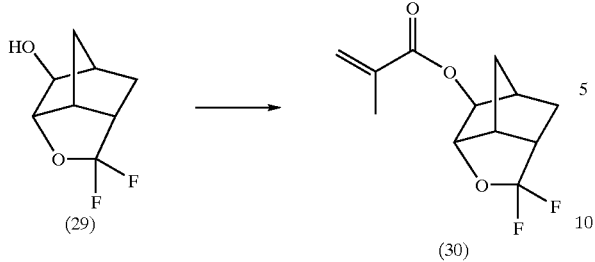

To a mixture of 4-hydroxy-6-oxatricyclo[3.2.1.1$^{3,8}$] nonan-7-one represented by Formula (27) (10 mmol) and toluene (50 ml) was added 2,4-bis(4-methoxyphenyl)-1,3,2, 4-dithiadiphosphetane 2,4-disulfide [(p-MeO-C$_6$H$_4$P (=S)—S—)$_2$)] (10 mmol), and the resulting mixture was stirred at 110° C. for 24 hours. The reaction mixture was concentrated, the concentrate was subjected to silica gel column chromatography and thereby yielded 4-hydroxy-6-oxatricyclo[3.2.1.1$^{3,8}$]nonane-7-thione represented by Formula (28) in a yield of 65%.

[Spectral Data of the Compound of Formula (28)]

MS m/e: 171 ([M$^+$]), 152, 120.

To a mixture of the cyclic thioester derivative represented by Formula (28) (2 mmol) obtained by the above procedure and dry methylene chloride (10 ml) was added a solution of diethylaminosulfur trifluoride (DAST) in methylene chloride (1 M solution, 4 ml, 2 equivalents) using a syringe at room temperature in an atmosphere of nitrogen gas, followed by stirring for 24 hours. After the completion of the reaction, the resulting mixture was washed with an aqueous sodium hydrogencarbonate solution, and the organic layer was concentrated. The concentrate was subjected to silica gel column chromatography and thereby yielded 7,7-difluoro-4-hydroxy-6-oxatricyclo[3.2.1.1$^{3,8}$]nonane represented by Formula (29) in a yield of 59%.

[Spectral Data of the Compound of Formula (29)]

MS m/e: 177 ([M$^+$]), 159, 141.

A mixture of the cyclic compound having a group containing a fluorine atom represented by Formula (29) (10 mmol) obtained by the above procedure, methacrylic acid (20 mmol), concentrated sulfuric acid (0.5 mmol), toluene (8 folds by volume that of the above three components), and hydroquinone (10000 ppm) was stirred for 8 hours under dehydration and reflux. After the completion of the reaction, the reaction mixture was concentrated, the concentrate was subjected to silica gel column chromatography and thereby yielded 7,7-difluoro-4-methacryloyioxy-6-oxatricyclo [3.2.1.1$^{3,8}$]nonane represented by Formula (30) in a yield of 82%.

[Spectral Data of the Compound of Formula (30)]

MS m/e: 245 ([M$^+$]) 160, 69.

Example 14

Production of 5-[1,1-bis(trifluoromethyl)-1-hydroxymethyl]oxybicyclo[2.2.1]-2-heptene According to the following reaction formula, 5-[1,1-bis (trifluoromethyl)-1-hydroxymethyl]oxybicyclo[2.2.1]-2-heptene was produced.

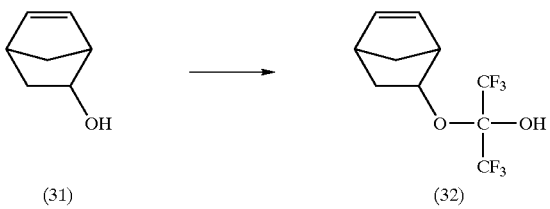

In a reactor equipped with a dry ice-ethanol reflux condenser was placed 5-hydroxybicyclo[2.2.1]-2-heptene (Formula (31), 50 mmol), and hexafluoroacetone gas (50 mmol) was blown thereinto while cooling on an ice bath. The resulting mixture was stirred at room temperature for further 1 hour and thereby yielded 5-[1,1-bis (trifluoromethyl)-1-hydroxymethyl]oxybicyclo[2.2.1]-2-heptene represented by Formula (32) in a yield of 95%.

[Spectral Data]

MS m/e: 277 (M+1), 259, 66.

$^{19}$F-NMR (CDCl$_3$) δ: −79.7.

Example 15

Production of 5-[1,1-bis(trifluoromethyl)-1-hydroxymethyl]oxymethylbicyclo[2.2.1]-2-heptene According to the following reaction formula, 5-[1,1-bis (trifluoromethyl)-1-hydroxymethyl]oxymethylbicyclo [2.2.1]-2-heptene was produced.

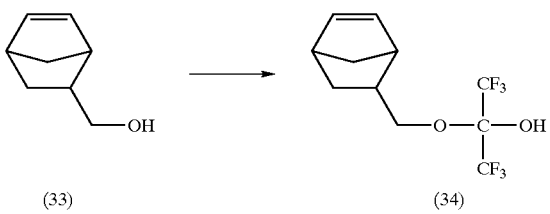

In a reactor equipped with a dry ice-ethanol reflux condenser was placed 5-hydroxymethylbicyclo[2.2.1]-2-heptene (Formula (33), 30 mmol), and hexafluoroacetone gas (30 mmol) was blown thereinto while cooling on an ice bath. The resulting mixture was stirred at room temperature for further 1 hour and thereby yielded 5-[1,1-bis (trifluoromethyl)-1-hydroxymethyl]oxymethylbicyclo [2.2.1]-2-heptene represented by Formula (34) in a yield of 97%.

[Spectral Data]

MS m/e: 291 (M+1), 273, 66.

Example 16

Production of 5-hydroxy-6-[1,1-bis (trifluoromethyl)-1-hydroxymethyl]oxybicyclo [2.2.1]-2-heptene]

According to the following reaction formula, 5-hydroxy-6-[1,1-bis(trifluoromethyl)-1-hydroxymethyl]oxybicyclo [2.2.1]-2-heptene was produced.

In a reactor equipped with a dry ice-ethanol reflux condenser was placed 5,6-dihydroxybicyclo[2.2.1]-2-heptene (Formula (35), 30 mmol), and hexafluoroacetone gas (30 mmol) was blown thereinto while cooling on an ice bath. The resulting mixture was stirred at room temperature for further 0.5 hour, the reaction mixture was subjected to silica gel column chromatography and thereby yielded 5-hydroxy-6-[1,1-bis(trifluoromethyl)-1-hydroxymethyl]oxybicyclo [2.2.1]-2-heptene represented by Formula (36) in a yield of 38%.

[Spectral Data]
MS m/e: 293 (M+1), 275, 68.

Example 17

Production of 2,2-difluoro-1,3-dioxolene

According to the following reaction formula, 2,2-difluoro-1,3-dioxolene represented by Formula (39) was produced.

To a mixture of 1,3-dioxolen-2-one represented by Formula (37) (50 mmol) and toluene (50 ml) was added 2,4-bis(4-methoxyphenyl)-1,3,2,4-dithiadiphosphetane 2,4-disulfide [(p-MeO-$C_6H_4$P(=S)—S—)$_2$)] (50 mmol), and the resulting mixture was stirred at 110° C. for 24 hours. The reaction mixture was concentrated, the concentrate was subjected to silica gel column chromatography and thereby yielded 1,3-dioxolene-2-thione represented by Formula (38) in a yield of 72%.

[Spectral Data of the Compound of Formula (38)]
MS m/e: 277 (M+1), 259, 66.
$^1$H-NMR (CDCl$_3$) δ: 6.62 (d, 2H).

To a mixture of the cyclic compound represented by Formula (38) (20 mmol) obtained by the above procedure and dry methylene chloride (30 ml) was added a solution of diethylaminosulfur trifluoride (DAST) in methylene chloride (1 M solution, 2 equivalents) at room temperature in an atmosphere of nitrogen gas, followed by stirring for 24 hours. After the completion of the reaction, the resulting mixture was washed with an aqueous sodium hydrogen carbonate solution, and the organic layer was concentrated. The concentrate was subjected to silica gel column chromatography and thereby yielded 2,2-difluoro-1,3-dioxolene represented by Formula (39) in a yield of 58%.

[Spectral Data of the Compound of Formula (39)]

MS m/e: 109 (M+1).

Example 18

Production of 2,2,5,5-tetrafluoro-1-oxolene

According to the following reaction formula, 2,2,5,5-tetrafluoro-1-oxolene represented by Formula (42) was produced.

To a mixture of maleic anhydride represented by Formula (40) (50 mmol) and toluene (30 ml) was added 2,4-bis(4-methoxyphenyl)-1,3,2,4-dithiadiphosphetane 2,4-disulfide [(p-MeO-$C_6H_4$P(=S)—S—)$_2$)] (50 mmol), and the resulting mixture was stirred at 110° C. for 24 hours. The reaction mixture was concentrated, the concentrate was subjected to silica gel column chromatography and thereby yielded 1-oxolene-2,5-dithione represented by Formula (41) in a yield of 21%.

[Spectral Data of the Compound of Formula (41)]

MS m/e: 131 (M+1).

To a mixture of the cyclic compound represented by Formula (41) obtained by the above procedure (5 mmol) and dry methylene chloride (10 ml) was added a solution of diethylaminosulfur trifluoride (DAST) in methylene chloride (1 M solution, 4 equivalents) at room temperature in an atmosphere of nitrogen gas, followed by stirring for 24 hours. After the completion of the reaction, the resulting mixture was washed with an aqueous sodium hydrogencarbonate solution, and the organic layer was concentrated. The concentrate was subjected to silica gel column chromatography and thereby yielded 2,2,5,5-tetrafluoro-1-oxolene represented by Formula (42) in a yield of 48%.

[Spectral Data of the Compound of Formula (42)]

MS m/e: 143 (M+1).

Example 19

Production of 2,2-difluoro-1,3-dithiolene

According to the following reaction formula, 2,2-difluoro-1,3-dithiolene represented by Formula (44) was produced.

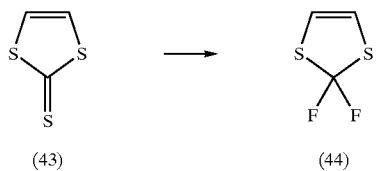

To a mixture of 1,3-dithiolene-2-thione (30 mmol) and dry methylene chloride (30 ml) was added a solution of diethylaminosulfur trifluoride (DAST) in methylene chloride (1 M solution, 2 equivalents) at room temperature in an atmosphere of nitrogen gas, followed by stirring for 24 hours. After the completion of the reaction, the resulting mixture was washed with an aqueous sodium hydrogencarbonate solution, and the organic layer was concentrated. The concentrate was subjected to silica gel column chromatography and thereby yielded 2,2-difluoro-1,3-dithiolene represented by Formula (44) in a yield of 37%.

[Spectral Data of the Compound of Formula (44)]

MS m/e: 141 (M+1).

$^1$H-NMR (CDCl$_3$) δ: 6.67 (d, 2H).

Example 20

Production of 8,8-difluoro-7,9-dithiatricyclo[4.3.0.1$^{2,5}$]-3-decene

According to the following reaction formula, 8,8-difluoro-7,9-dithiatricyclo[4.3.0.1$^{2,5}$]-3-decene represented by Formula (46) was produced.

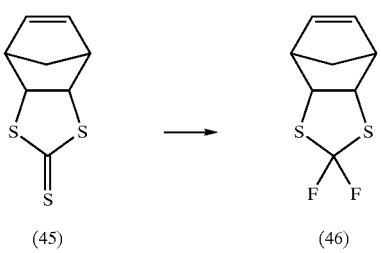

To a mixture of 7,9-dithiatricyclo[4.3.0.1$^{2,5}$]-3-decene-8-thione represented by Formula (45) (10 mmol) and dry methylene chloride (20 ml) was added a solution of diethylaminosulfur trifluoride (DAST) in methylene chloride (1 M solution, 2 equivalents) at room temperature in an atmosphere of nitrogen gas, followed by stirring for 24 hours. After the completion of the reaction, the resulting mixture was washed with an aqueous sodium hydrogencarbonate solution, and the organic layer was concentrated. The concentrate was subjected to silica gel column chromatography and thereby yielded 8,8-difluoro-7,9-dithiatricyclo[4.3.0.1$^{2,5}$]-3-decene represented by Formula (46) in a yield of 67%.

[Spectral Data of the Compound of Formula (46)]

MS m/e: 207 (M+1), 66.

Example 21

Production of 5-[1-trifluoromethyl-1-hydroxy-1-(norborn-2-yl)methyl]bicyclo[2.2.1]-2-heptene According to the following reaction formula, 5-[1-trifluoromethyl-1-hydroxy-1-(norborn-2-yl)methyl]bicyclo[2.2.1]-2-heptene was produced.

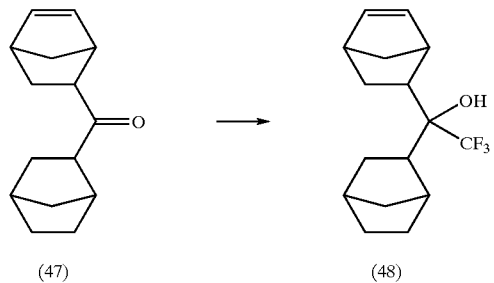

A mixture of 5-(norborn-2-ylcarbonyl)bicyclo[2.2.1]-2-heptene (Formula (47), 10 mmol), trimethyl(trifluoromethyl)silane [TMS-CF$_3$] (12 mmol), and dry tetrahydrofuran (THF) (20 ml) was treated with a 1-M solution of tetrabutylammonium fluoride in THF (0.05 equivalent) in an atmosphere of nitrogen gas for 2 hours while cooling on ice bath and stirring, and the resulting mixture was stirred at room temperature for further 20 hours. The mixture was treated with 1 N hydrochloric acid with stirring for 20 hours. The reaction mixture was concentrated, the concentrate was subjected to silica gel column chromatography and thereby yielded 5-[1-trifluoromethyl-1-hydroxy-1-(norborn-2-yl)methyl]bicyclo[2.2.1]-2-heptene represented by Formula (48) in a yield of 87%.

[Spectral Data]

MS m/e: 289 (M+1), 271, 69.

Example 22

Production of 5-(1-trifluoromethyl-1-hydroxyethyl)bicyclo[2.2.1]-2-heptene and 5-(1-trifluoromethyl-1-trimethylsilyloxyethyl)bicyclo[2.2.1]-2-heptene According to the following reaction formula, 5-(1-trifluoromethyl-1-hydroxyethyl)bicyclo[2.2.1]-2-heptene and 5-(1-trifluoromethyl-1-trimethylsilyloxyethyl)bicyclo[2.2.1]-2-heptene were produced. In the formula, TMS represents a trimethylsilyl group.

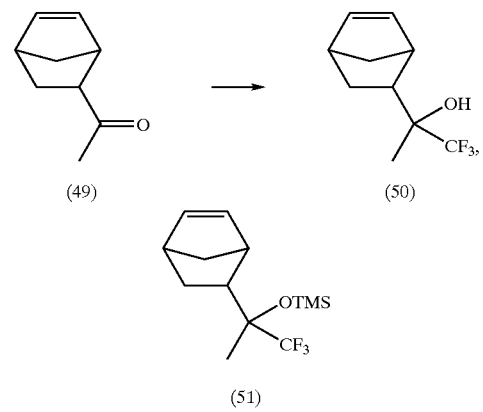

A mixture of 5-acetylbicyclo[2.2.1]-2-heptene (Formula (49), 50 mmol), trimethyl(trifluoromethyl)silane [TMS- CF₃] (60 mmol), and dry tetrahydrofuran (THF) (100 ml) was treated with a 1-M solution of tetrabutylammonium fluoride in THF (0.05 equivalent) in an atmosphere of nitrogen gas for 2 hours while cooling on ice bath and stirring, and the resulting mixture was stirred at room temperature for further 20 hours. The reaction mixture was concentrated, the concentrate was subjected to silica gel column chromatography and thereby yielded 5-(1-trifluoromethyl-1-hydroxyethyl)bicyclo[2.2.1]-2-heptene represented by Formula (50) in a yield of 5% and 5-(1-trifluoromethyl-1-trimethylsilyloxyethyl)bicyclo[2.2. 1]-2-heptene represented by Formula (51) in a yield of 81%.

A solution of the above-prepared 5-(1-trifluoromethyl-1-trimethylsilyloxyethyl)bicyclo[2.2. 1]-2-heptene represented by Formula (51) (35 mmol) in acetone (50 ml) was treated with 3 N hydrochloric acid with stirring for 20 hours. The reaction mixture was concentrated, the concentrate was subjected to silica gel column chromatography and thereby yielded 5-(1-trifluoromethyl-1-hydroxyethyl)bicyclo [2.2.1]-2-heptene represented by Formula (50) in a yield of 93%.

[Spectral Data of the Compound of Formula (50)]

MS m/e: 207 (M+1), 189, 163, 66.

¹⁹F-NMR (CDCl₃) δ: −81.8.

¹H-NMR (CDCl₃) δ: 6.28 (dd, 1H), 6.08 (dd, 1H), 3.03 (brs, 1H), 2.88 (brs, 1H), 2.52 (m, 1H), 1.93 (m, 1H), 1.83 (s, 1H), 1.50–1.20 (m, 6H).

[Spectral Data of the Compound of Formula (51)]

MS m/e: 279 (M+1), 263, 189, 167, 66.

Example 23

Production of 5-[1-trifluoromethyl-1-(1-ethoxyethyloxy)ethyl]bicyclo[2.2.1]-2-heptene]

According to the following reaction formula, 5-[1-trifluoromethyl-1-(1-ethoxyethyloxy)ethyl]bicyclo[2.2.1]-2-heptene was produced.

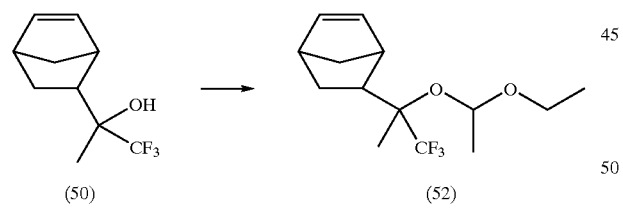

A mixture of 5-(1-trifluoromethyl-1-hydroxyethyl)bicyclo[2.2.1]-2-heptene represented by Formula (50) obtained in Example 22 (20 mmol), ethyl vinyl ether (22 mmol) and methylene chloride (50 ml) was treated with p-toluenesulfonic acid (0.4 mmol) at room temperature for 5 hours with stirring. The reaction mixture was washed with an aqueous sodium hydrogencarbonate solution, the organic layer was concentrated, the concentrate was subjected to silica gel column chromatography and thereby yielded 5-[1-trifluoromethyl-1-(1-ethoxyethyloxy)ethyl]bicyclo[2.2.1]-2-heptene represented by Formula (52) in a yield of 87%.

[Spectral Data]

MS m/e: 315 (M+1), 225, 66.

Example 24

Synthesis of a Polymer having the Following Structure

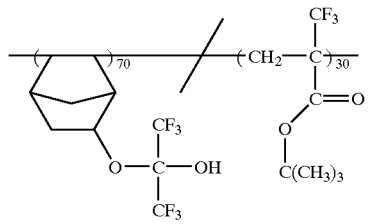

In a 100-ml egg plant type flask equipped with a reflux condenser were placed 5-[1,1-bis(trifluoromethyl)-1-hydroxymethyl]oxabicyclo[2.2.1]-2-heptene represented by Formula (32) (21 mmol), t-butyl 2-trifluoromethylacrylate (9 mmol), and dry tetrahydrofuran (25 ml), and the resulting mixture was treated with AIBN (2,2'-azobisisobutyronitrile) (500 mg) at a temperature of 60° C. to 65° C. in an atmosphere of argon gas for 2 hours with stirring. After standing to cool, the reaction mixture was poured onto methanol, the deposited precipitate was collected by filtration, was then subjected to the precipitation and purification procedure again and thereby yielded the target polymer in a yield of 43%. The polymerization ratio in the polymer was determined based on the signal ratio in ¹H-NMR and was found to be 70:30 as shown in the structural formula. The polymer had a weight average molecular weight of 10700 in terms of polystyrene and a molecular weight distribution (Mw/Mn) of 2.25 as determined by GPC analysis.

Example 25

Synthesis of a Polymer Having the Following Structure

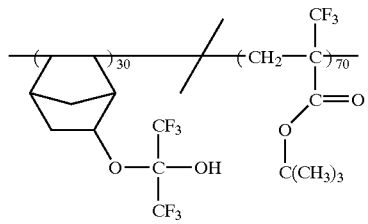

In a 100-ml egg plant type flask equipped with a reflux condenser were placed 5-[1,1-bis(trifluoromethyl)-1-hydroxymethyl]oxabicyclo[2.2.1]-2-heptene represented by Formula (32) (9 mmol), t-butyl 2-trifluoromethylacrylate (21 mmol), and dry tetrahydrofuran (25 ml), and the resulting mixture was treated with AIBN (2,2'-azobisisobutyronitrile) (500 mg) at 60° C. to 65° C. in an atmosphere of argon gas for 2 hours with stirring. After standing to cool, the reaction mixture was poured onto methanol, the deposited precipitate was collected by filtration, was then subjected to the precipitation and purification procedure and thereby yielded the target polymer in a yield of 53%. The polymerization ratio in the polymer was determined based on the signal ratio in ¹H-NMR and was found to be 30:70 as shown in the structural formula. The polymer had a weight average molecular weight of 11800 in terms of polystyrene as determined by GPC analysis.

Example 26

Synthesis of a Polymer having the Following Structure

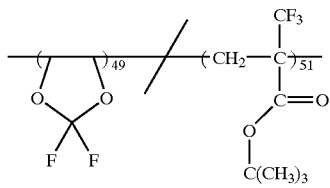

In a 100-ml egg plant type flask equipped with a reflux condenser were placed 2,2-difluoro-1,3-dioxolene represented by Formula (39) (15 mmol), t-butyl 2-trifluoromethylacrylate (15 mmol), and dry tetrahydrofuran (25 ml), and the resulting mixture was treated with AIBN (2,2'-azobisisobutyronitrile) (500 mg) at a temperature of 60° C. to 65° C. in an atmosphere of argon gas for 2 hours with stirring. After standing to cool, the reaction mixture was poured onto methanol, the deposited precipitate was collected by filtration, was then subjected to the precipitation and purification procedure again and thereby yielded the target polymer in a yield of 41%. The polymerization ratio in the polymer was determined based on the signal ratio in $^1$H-NMR and was found to be 49:51 as shown in the structural formula. The polymer had a weight average molecular weight of 9600 in terms of polystyrene and a molecular weight distribution (Mw/Mn) of 1.92 as determined by GPC analysis.

Example 27

Synthesis of a Polymer having the Following Structure

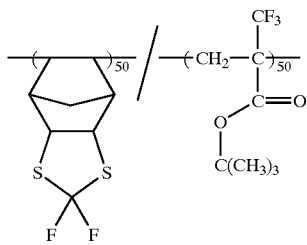

In a 100-ml egg plant type flask equipped with a reflux condenser were placed 8,8-difluoro-7,9-dithiatricyclo[4.3.0.1$^{2,5}$]-3-decene represented by Formula (46) (15 mmol), t-butyl 2-trifluoromethylacrylate (15 mmol), and dry tetrahydrofuran (25 ml), and the resulting mixture was treated with AIBN (2,2'-azobisisobutyronitrile) (500 mg) at a temperature of 60° C. to 65° C. in an atmosphere of argon gas for 2 hours with stirring. After standing to cool, the reaction mixture was poured onto methanol, the deposited precipitate was collected by filtration, was then subjected to the precipitation and purification procedure again and thereby yielded the target polymer in a yield of 51%. The polymerization ratio in the polymer was determined based on the signal ratio in $^1$H-NMR and was found to be 50:50 as shown in the structural formula. The polymer had a weight average molecular weight of 9600 in terms of polystyrene and a molecular weight distribution (Mw/Mn) of 1.79 as determined by GPC analysis.

Example 28

Synthesis of a Polymer having the Following Structure

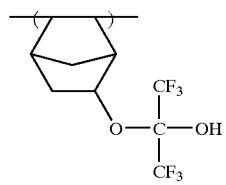

In a 100-ml egg plant type flask equipped with a reflux condenser were placed 5-[1,1-bis(trifluoromethyl)-1-hydroxymethyl]oxybicyclo[2.2.1]-2-heptene represented by Formula (32) (30 mmol) and dry tetrahydrofuran (25 ml), and the resulting mixture was treated with AIBN (2,2'-azobisisobutyronitrile) (500 mg) at a temperature of 60° C. to 65° C. in an atmosphere of argon gas for 2 hours with stirring. After standing to cool, the reaction mixture was poured onto methanol, the deposited precipitate was collected by filtration, was then subjected to the precipitation and purification procedure again and thereby yielded the target polymer in a yield of 51%.

TEST EXAMPLE

Determination of Pattering by a Resist Using the Polymer

A resist (a photosensitive resin composition) having the following composition was prepared.

(a) Polymer (Example 1): 100 parts by weight (b) Triphenylsulfonium trifluoromethanesulfonate: 2 parts by weight (c) Additive (triethanolamine): 0.1 part by weight The above components (a), (b), and (c) were dissolved in 2000 parts by weight of propylene glycol monomethyl ether monoacetate, the resulting solution was filtrated through a membrane filter having a pore size of 0.1 μm and thereby yielded a resist. The resist was applied to an 4-inch silicon substrate by spin coating, was dried on a hot plate at 90° C. for 90 seconds and thereby yielded a resist layer 0.4 μm thick. The resist layer was irradiated with ArF excimer laser light through a mask using an exposure system. The exposed resist layer was then immediately heated at 110° C. for 90 seconds, was developed by dipping in a 2.38% by weight tetramethylammonium hydroxide aqueous solution for 60 seconds, was subsequently rinsed with pure water for 60 seconds and thereby yielded a positive resist pattern. In this procedure, the exposure at which a 0.20-μm line-and-space pattern was obtained was 9 mJ/cm$^2$.

What is claimed is:

1. A monomer containing an electron-withdrawing group, represented by following Formula (b) or (c):

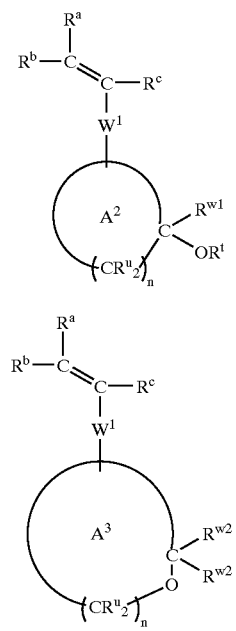

wherein $A^2$, and $A^3$ are each a ring; $R^a$, $R^b$, $R^c$, and $R^u$ are the same or different and are each a hydrogen atom or an organic group; at least one of $R^t$ and $R^{w1}$, and at least one of the two $R^{w2}$s are each an electron-withdrawing group, and the others are each a hydrogen atom or an organic group; $W^1$ is a single bond or a linkage group; and n denotes an integer of from 2 to 25, where at least two of $R^a$, $R^b$, $R^c$, $R^t$, $R^u$, $R^{w1}$, $R^{w2}$, $W^1$, carbon atoms constituting ring $A^2$, and carbon atoms constituting ring $A^3$ may be combined to form a ring, respectively.

2. The monomer containing an electron-withdrawing group according to claim 1, wherein the electron-withdrawing groups in $R^t$, $R^{w1}$, and $R^{w2}$ are group containing a fluorine atom.

3. The monomer containing an electron-withdrawing group according to claim 1, wherein ring $A^2$ or ring $A^3$ is a monocyclic ring or bridged ring containing at least a 5- to 7-membered carbocyclic ring or oxygen-containing heterocyclic ring.

4. The monomer containing an electron-withdrawing group according to claim 1, having a bridged ring skeleton, the bridged ring skeleton including ring $A^2$ or ring $A^3$ and containing 7 to 15 carbon atoms.

5. A process for producing a monomer containing an electron-withdrawing group, the process comprising the step of allowing a cyclic ketone having an ethylenic double bond, represented by following Formula (d):

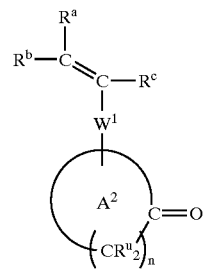

wherein $A^2$ is a ring; $R^a$, $R^b$, $R^c$ and $R^u$ are the same or different and are each a hydrogen atom or an organic group; $W^1$ is a single bond or a linkage group; and n denotes an integer of from 2 to 25, where at least two of $R^a$, $R^b$, $R^c$, $R^u$, $W^1$, and carbon atoms constituting ring $A^2$ may be combined to form a ring, respectively, to react with a fluorine reagent, or subjecting the cyclic ketone having an ethylenic double bond represented by Formula (d) to a reaction with the fluorine reagent and to a subsequent reaction for introducing a protecting group to thereby yield a monomer containing a fluorine atom and having an ethylenic double bond, represented by following Formula (b1):

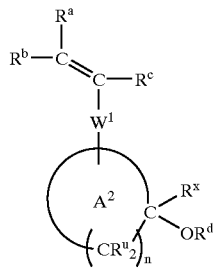

wherein $R^x$ is a group containing a fluorine atom; $R^d$ is a hydrogen atom or a hydroxyl-protecting group; $A^2$, $R^a$, $R^b$, $R^c$, $R^u$, $W^1$, and n have the same meanings as defined above, where at least two of $R^a$, $R^b$, $R^c$, $R^u$, $W^1$, and carbon atoms constituting ring $A^2$ may be combined to form a ring, respectively.

6. A process for producing a monomer containing an electron-withdrawing group, the process comprising the step of allowing a cyclic thioester having an ethylenic double bond, represented by following Formula (e):

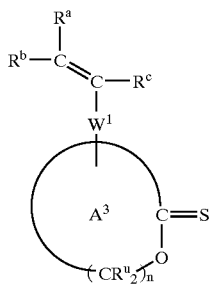

wherein $A^3$ is a ring; $R^a$, $R^b$, $R^c$, and $R^u$ are the same or different and are each a hydrogen atom or an organic group; $W^1$ is a single bond or a linkage group; and n denotes an integer of from 2 to 25, where at least two of $R^a$, $R^b$, $R^c$, $R^u$, $W^1$, and carbon atoms constituting ring $A^3$ may be combined to form a ring, respectively, to react with a fluorine reagent to thereby yield a monomer containing a fluorine atom and having an ethylenic double bond, represented by following Formula (c1):

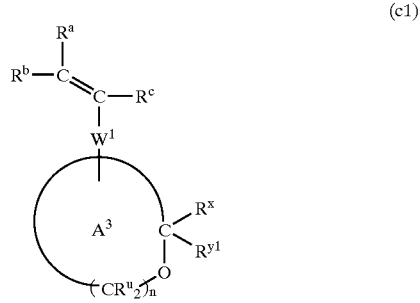

(c1)

wherein $R^x$ and $R^{y1}$ are each a group containing a fluorine atom; $A^3$, $R^a$, $R^b$, $R^c$, $R^u$, $W^1$, and n have the same meanings as defined above, where at least two of $R^a$, $R^b$, $R^c$, $R^u$, $W^1$, and carbon atoms constituting ring $A^3$ may be combined to form a ring, respectively.

7. A process for producing a monomer containing an electron-withdrawing group, the process comprising the step of allowing a cyclic compound containing an acyl group and having an ethylenic double bond, represented by following Formula (f):

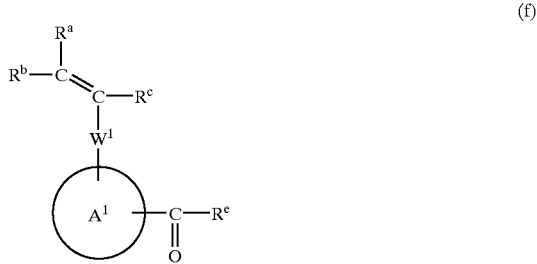

(f)

wherein $A^1$ is a ring; $R^a$, $R^b$, $R^c$, and $R^e$ are the same or different and are each a hydrogen atom or an organic group; $W^1$ is a single bond or a linkage group, where at least two of $R^a$, $R^b$, $R^c$, $R^e$, $W^1$, and carbon atoms constituting ring $A^1$ may be combined to form a ring, respectively, to react with a fluorine reagent, or subjecting the cyclic compound containing an acyl group and having an ethylenic double bond represented by Formula (f) to a reaction with the fluorine reagent and to a subsequent reaction for introducing a protecting group to thereby yield a monomer containing a fluorine atom and having an ethylenic double bond, represented by following Formula (a1):

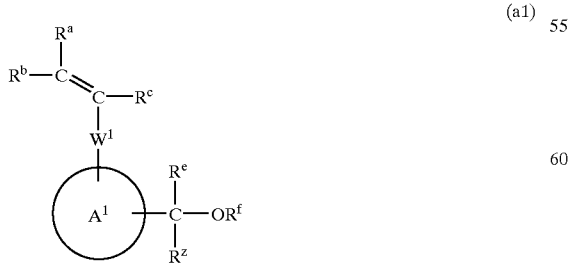

(a1)

wherein $R^z$ is a group containing a fluorine atom; $R^f$ is a hydrogen atom or a hydroxyl-protecting group; and $A^1$, $R^a$, $R^b$, $R^c$, $R^e$, and $W^1$ have the same meanings as defined above, where at least two of $R^a$, $R^b$, $R^c$, $R^e$, $W^1$, and carbon atoms constituting ring $A^1$ may be combined to form a ring, respectively.

8. A monomer containing an electron-withdrawing group, represented by following Formula (a):

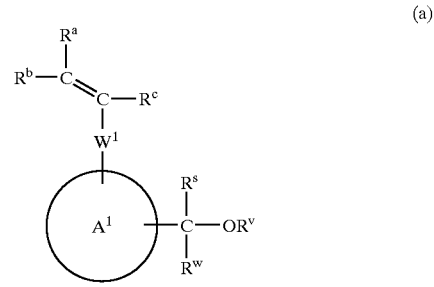

(a)

wherein $A^1$ is a ring; $R^a$, $R^b$, and $R^c$ are the same or different and are each a hydrogen atom or an organic group; at least one of $R^s$, $R^w$ and $R^v$ is an electron-withdrawing group, and the others are each a hydrogen atom or an organic group; $W^1$ is a single bond or a linkage group; where at least two of $R^a$, $R^b$, $R^c$, $R^s$, $R^v$, $R^w$, $W^1$, carbon atoms constituting ring $A^1$ may be combined to form a ring, respectively; with the proviso that when at least one of the carbon atoms constituting ring $A^1$ are combined with $R^a$ or $R^b$ to form a ring, then $R^v$ is at least one selected from the group consisting of a hydrogen, a hydrocarbon group, a heterocyclic group, an alkoxycarbonyl group, an aryloxycarbonyl group, an acyl group, a cyano group, and a nitro group, wherein the heterocyclic group is substituted or unsubstituted, and wherein the hydrocarbon group is unsubstituted or is substituted by at least on substituent selected from a group consisting of oxo group, hydroxyl group which may be protected by a protecting group, hydroxymethyl group which may be protected by a protecting group, amino group which may be protected by a protecting group, carboxyl group which may be protected by a protecting group, substituted oxycarbonyl group, substituted or unsubstituted carbamoyl group, nitro group, acyl group, cyano group, aryl group, and a heterocyclic group.

9. A monomer containing an electron-withdrawing group, represented by following Formula (a):

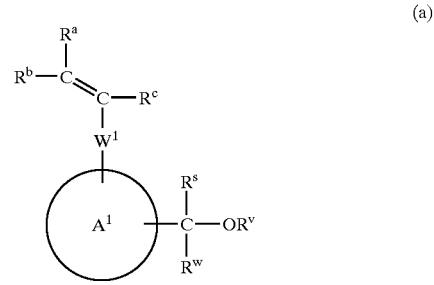

(a)

wherein $A^1$ is a ring; $R^a$, $R^b$, and $R^c$ are the same or different and are each a hydrogen atom or an organic group; a least one of $R^s$ and $R^w$ is an electron-withdrawing group, a hydrogen atom or an organic group; $R^v$ is an electron-withdrawing group; $W^1$ is a single bond or a linkage group; where at least two of $R^c$, $R^s$, $R^v$, $R^w$, $W^1$, carbon atoms constituting ring $A^1$ may be combined to form a ring, respectively.

10. The monomer containing an electron-withdrawing group according to claim 8 or 9, wherein the electron-withdrawing groups in $R^s$, $R^v$, and $R^w$, are group containing a fluorine atom.

11. The monomer containing an electron-withdrawing group according to claim 8 or 9, wherein ring $A^1$ is a monocyclic ring or bridged ring containing at least a 5- to 7-membered carbocyclic ring or oxygen-containing heterocyclic ring.

12. The monomer containing an electron-withdrawing group according to claim 8 or 9, having a bridged ring skeleton, the bridged ring skeleton including ring $A^1$ and containing 7 to 15 carbon atoms.

* * * * *